US009386950B1

(12) United States Patent
Almack

(10) Patent No.: US 9,386,950 B1
(45) Date of Patent: Jul. 12, 2016

(54) SYSTEMS AND METHODS FOR DETECTING DYSLEXIA

(71) Applicant: Online Reading Tutor Services Inc., Blackstock (CA)

(72) Inventor: Robert Almack, Blackstock (CA)

(73) Assignee: Online Reading Tutor Services Inc., Ontario (CA)

(*) Notice: Subject to any disclaimer, the term of this patent is extended or adjusted under 35 U.S.C. 154(b) by 0 days.

(21) Appl. No.: 14/585,253

(22) Filed: Dec. 30, 2014

(51) Int. Cl.
*A61B 5/00* (2006.01)
*A61B 3/02* (2006.01)
*A61B 3/00* (2006.01)

(52) U.S. Cl.
CPC .............. *A61B 5/4088* (2013.01); *A61B 3/0033* (2013.01); *A61B 3/02* (2013.01); *A61B 5/0022* (2013.01); *A61B 5/6898* (2013.01); *A61B 5/7275* (2013.01); *A61B 5/7435* (2013.01)

(58) Field of Classification Search
CPC .... A61B 3/0058; A61B 3/032; A61B 5/0484; A61B 5/04845; G06F 19/345
See application file for complete search history.

(56) References Cited

U.S. PATENT DOCUMENTS

| | | | | |
|---|---|---|---|---|
| 3,952,728 | A * | 4/1976 | Levinson et al. | 600/300 |
| 4,706,686 | A * | 11/1987 | Levinson | A61B 3/02 351/237 |
| 5,057,020 | A * | 10/1991 | Cytanovich | 434/178 |
| 5,577,919 | A * | 11/1996 | Collins et al. | 434/322 |
| 5,813,862 | A * | 9/1998 | Merzenich et al. | 434/185 |
| 5,951,298 | A * | 9/1999 | Werzberger | 434/178 |
| 6,056,551 | A * | 5/2000 | Marasco | 434/178 |
| 6,155,834 | A * | 12/2000 | New, III | 434/118 |
| 6,299,452 | B1 * | 10/2001 | Wasowicz et al. | 434/178 |
| 6,382,791 | B1 * | 5/2002 | Strawderman et al. | 351/203 |
| 8,497,868 | B2 * | 7/2013 | Lopez | G09G 3/006 345/581 |
| 2002/0076675 | A1 * | 6/2002 | Budra et al. | 434/167 |
| 2002/0119429 | A1 * | 8/2002 | Barton | 434/178 |
| 2004/0058306 | A1 * | 3/2004 | Wiig et al. | 434/362 |
| 2005/0069848 | A1 * | 3/2005 | Cytanovich | 434/178 |
| 2007/0099158 | A1 * | 5/2007 | Moran et al. | 434/156 |
| 2007/0248938 | A1 * | 10/2007 | Ronald | 434/178 |
| 2008/0039698 | A1 * | 2/2008 | Burton | 600/300 |
| 2009/0189775 | A1 * | 7/2009 | Lashina et al. | 340/825.36 |
| 2009/0231273 | A1 * | 9/2009 | Lashina et al. | 345/156 |
| 2010/0253905 | A1 * | 10/2010 | Lawton | 351/203 |
| 2010/0306657 | A1 * | 12/2010 | Derbyshire | G06F 17/30749 715/727 |
| 2011/0010671 | A1 * | 1/2011 | Harma | G11B 27/105 715/835 |
| 2012/0236201 | A1 * | 9/2012 | Larsen et al. | 348/468 |
| 2012/0266067 | A1 * | 10/2012 | Armstrong | H04S 5/005 715/716 |
| 2013/0173287 | A1 * | 7/2013 | Cashman | E04H 3/08 705/2 |
| 2014/0093855 | A1 * | 4/2014 | Waldman | G09B 5/065 434/308 |

FOREIGN PATENT DOCUMENTS

JP 2012185323 A * 9/2012

* cited by examiner

*Primary Examiner* — Sean Dougherty
(74) *Attorney, Agent, or Firm* — Finnegan, Henderson, Farabow, Garrett & Dunner, LLP

(57) ABSTRACT

The present disclosure is directed to systems and methods for determining an individual's risk of dyslexia. A plurality of query pages may be rendered. Each query page may comprise a plurality of non-verbal answers that are selectable by the user. A plurality of auditory queries may be rendered. Each auditory query may comprise sound data corresponding to a non-verbal query. Each auditory query may be associated with one or more of the plurality of query pages. A plurality of selections may be received from the user. Each selection may identify a non-verbal answer from a query page. An assessment may be generated. The assessment may identify a user's risk of dyslexia based on the plurality of selections and timing data that indicates how much time the user took to make each of the plurality of selections.

18 Claims, 28 Drawing Sheets

300

Dyslexia Test

301

302

If your believe your child may have a reading disability or dyslexia, the Online Reading Tutor screener can help identify specific reading problems and recommend an effective training program that will help your child develop fluent, automatic decoding skills. When reading becomes automatic or fluent, comprehension improves dramatically.

The screener only takes 5 to 10 minutes to complete. You will be provided with immediate results of the assessment. The assessment measures both processing speed and accuracy. If the student takes too long to answer, the question will be incorrect.

Name:

[            ] — 303

Select grade level ▽ — 303

Assessment Complete!

Minimum Expected Accuracy — 2302

Name — 2303

Name reads letter patterns with ____% accuracy. — 2304

Fluent readers names age are able to decode these letter patterns with an accuracy of 94% or above. At Online Reading Tutor, your child will be trained to this level of reading proficiency, resulting in improved reading comprehension. Fill in the next screen and we will receive details of your assessment, and one of our reading specialists will be pleased to contact you with more information — 2305

2306 — Start Again

Your Name:
[                    ] —2402

Your Phone:
[                    ] —2403

Your Email:
[                    ] —2404

Country:
[                 ▽] —2405

I am a:
(●) Parent   ( ) Teacher   ( ) Student  —2406

Fig. 24A

SYSTEMS AND METHODS FOR DETECTING DYSLEXIA

BACKGROUND

Dyslexia affects scores of people around the world. The disorder is generally characterized by a difficulty comprehending patterns of letters and the sounds that they make, despite a normal level of intelligence and physical ability. Those afflicted with dyslexia often have trouble with spelling, reading, rhyming, and articulating letter sounds.

Dyslexia generally involves a phonological ineptitude, which is a difficulty understanding and decoding letter sounds. Those who have dyslexia are unable to effectively identify letter sounds and communicate with them, such as by reading and writing. A specific example of a phonological difficulty is trouble with phonemes, the smallest elements of speech that convey a unique meaning. Commonly, dyslexics may make reading errors such as phonetic and mirror image errors. Phonetic errors may occur, for example, when an individual cannot match a sound that they hear to a pattern of letters that they see. For example, if a person hears the word "flat," they may confuse it with the word "falt," when viewed on paper. Mirror image errors may occur when a person confuses two words that are spelled backwards with respect to each other. For example, a person with mirror image difficulties may confuse "tag" and "gat."

While the precise cause of dyslexia is debated, it is commonly accepted that early detection of the disorder combined with specialized education can greatly improve the verbal abilities, such as reading comprehension, of dyslexics. Unfortunately, the symptoms of dyslexia are often not detected, or are confused with other learning disabilities. When the symptoms are not detected, those suffering from dyslexia are forced to cope with the disorder without treatments that could significantly improve their verbal abilities. When dyslexia is mistaken for a different learning disability or disorder, ineffective treatments may be given and medication may be used unnecessarily.

The prospects of improving a dyslexic's verbal abilities are greatest if the disorder is detected at an early age. If the disorder is detected in an individual's childhood, when the language areas of the brain are still developing, the effectiveness of treatment is highest. Furthermore, detecting dyslexia early in life allows an individual with the disorder to benefit from treatment at an early age, which provides benefits in both educational and social contexts. Presently, however, common techniques for detecting dyslexia are expensive, hard to obtain, and sometimes difficult to access.

SUMMARY

Described herein are systems and methods for determining a user's risk of dyslexia. Some embodiments may involve a computer-implemented method comprising a plurality of operations, each operation being performed using at least one computer processor device. The method may comprise rendering a plurality of query pages, each query page comprising a plurality of non-verbal answers that are selectable by the user. The method may also comprise rendering a plurality of auditory queries, each auditory query comprising sound data corresponding to a non-verbal query, each auditory query being associated with one or more of the plurality of query pages. Further, the method may comprise identifying a plurality of selections from the user, each selection identifying a non-verbal answer from a query page. In addition, the method may comprise rendering an assessment, the assessment identifying a risk of dyslexia for the user based on the plurality of selections and timing data, the timing data relating to amounts of time the user took to make each of the plurality of selections.

Additional embodiments may involve a computer-readable medium comprising a plurality of instructions that, when executed by at least one computer processor device, perform a method of determining a user's risk of dyslexia. The computer-readable medium may comprise instructions for generating a plurality of query pages, each query page comprising a plurality of non-verbal answers that are selectable by the user. The computer-readable medium may also comprise instructions for generating a plurality of auditory queries, each auditory query comprising sound data corresponding to a non-verbal query, each auditory query being associated with one or more of the plurality of query pages. Further, the computer-readable medium may comprise instructions for identifying a plurality of selections from the user, each selection identifying a non-verbal answer from a query page. In addition, the computer-readable medium may comprise instructions for generating an assessment, the assessment identifying a risk of dyslexia for the user based on the plurality of selections and timing data, the timing data relating to amounts of time the user took to make each of the plurality of selections.

The foregoing background and summary are not intended to be comprehensive, but instead serve to help artisans of ordinary skill understand the following implementations consistent with the invention set forth in the appended claims. In addition, the foregoing background and summary are not intended to provide any independent limitations on the claimed invention.

BRIEF DESCRIPTION OF DRAWINGS

The accompanying drawings, which are incorporated in and constitute a part of this disclosure, illustrate various embodiments and aspects of the present invention as set forth in the attached claims. In the drawings:

FIG. 3 depicts an exemplary identification page consistent with embodiments described herein.

FIG. 23 depicts an exemplary assessment page consistent with embodiments described herein.

FIG. 24A depicts an exemplary first feedback page consistent with embodiments described herein.

DETAILED DESCRIPTION

Reference will now be made in detail to the exemplary embodiments of the present disclosure, examples of which are illustrated in the accompanying drawings. Wherever possible, the same reference numbers will be used throughout the drawings to refer to the same or like parts.

Figure 1:
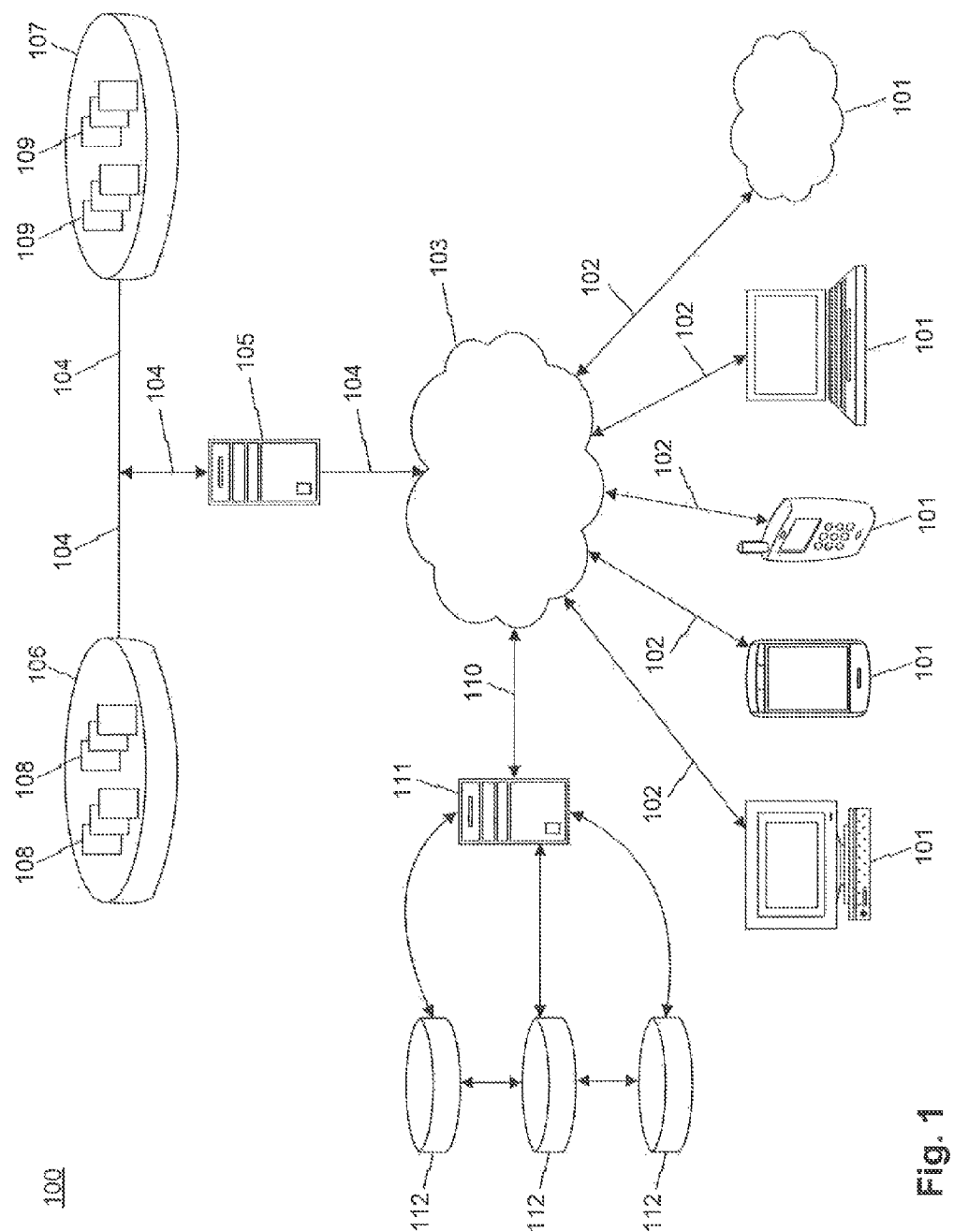
FIG. 1 depicts an exemplary system in which the embodiments described herein may be implemented.

Embodiments described herein may be implemented in a computer-based system 100, such as that shown in FIG. 1. System 100, in various embodiments, may comprise some or all of client devices 101, which may be personal computers, tablets, telephonic devices, or networks comprising such devices. Other types of computing devices may also be used as client devices 101.

Client devices 101 may each comprise one or more memories (e.g., random access memory, read only memory, flash memory, etc.) and one or more processors (e.g., microprocessors, microcontrollers, etc., such as an INTEL CORE processor or an AMD processor). Client devices 101 may each run one or more operating systems, such as a personal computer operating system (e.g., a WINDOWS or APPLE operating system) or a mobile operating system (e.g., an ANDROID or APPLE operating system). Client devices 101 may also have network connectivity, such as by a wired connection (e.g., Ethernet, USB, etc.) or a wireless connection (e.g., WiFi, etc.). As such, client devices 101 may be capable of both transmitting and receiving data over networks, such as local area networks and wide area networks, and storing both data and client applications. Client devices 101, and the data and applications that they host, may be manipulated with input devices such as mice, capacitive touchscreens, other touch-enabled selection devices, voice-control interfaces, stylus pens, etc.

Client devices 101 may send and receive data to, and through, networks 103 such as the Internet, other wide area networks, local area networks, etc., using communication paths 102. Accordingly, client devices 101 may communicate with other client devices across network 103, servers hosting Internet content (e.g., HTML pages, Java applications, XML data, videos, music, images, etc.), and other network-connected devices.

In some embodiments, client devices 101 may communicate with servers such as server 105. Server 105 may be a single computing device or a plurality of such devices (e.g., a server farm). Similar to client devices 101, server 105 may comprise one or more memories and one or more processors, such as an INTEL CORE processor or an AMD processor. Server 105 may also store both data and applications which run on server 105.

Server 105 may comprise software for exchanging data with databases, such as databases 106 and 107. Consistent with embodiments described herein, database 106 may comprise a plurality of query pages 108 and database 107 may comprise a plurality of auditory files 109 that correspond to the query pages. In some embodiments, databases 106 and 107 may comprise the same, single storage medium. In other embodiments, databases 106 and 107 may each comprise one or more storage media. Databases 106 and 107 may comprise memory for storing data and applications, and may be structured or unstructured. Data and applications from databases 106 and 107 may be accessed using various types of database queries. In some embodiments, databases 106 and 107 are physically separate from server 105, and in other embodiments databases and 106 and 107 are included in the same physical device as server 105. Server 105 may communicate with databases 106 and 107 via communication paths 104, and databases 106 and 107 may use the same or different communication paths 104 to communicate with each other.

In some embodiments, system 100 may include a server 111. Similar to server 105, server 111 may comprise one or more memories and one or more processors (e.g., an INTEL CORE processor or an AMD processor). Server 111 may be configured to store data and applications, such as applications for mobile devices or personal computers (e.g., clients 101). As with server 105, server 111 may be one or more physically separate servers, and may be a logically connected group of servers. Server 111 may communicate with databases 112, which may be configured to store applications. Databases 112 may be physically separate from each other, or included in the same physical device. Upon a request from a client (e.g., client 101), server 111 may access an application from a database 112 and send the application to the client. The application may then be executed on the client. In such an embodiment, the application would run locally on the client (e.g., using memory and processing associated with the client). In some embodiments, applications are pushed to clients (e.g., without any client request), from server 111 and database 112. In further embodiments, applications may run from server 111 or databases 112, with data corresponding to the running application being sent to the client (e.g., client 101). In such an embodiment, the application would be running remotely from the perspective of the client, whereby the client controls the running application without using its own storage and/or processing resources to run the application.

In some embodiments, server 105 and 111 may be hosted by the same service provider (e.g., a website provider, a mobile application provider, a third-party content provider or hosting service, etc.). Servers 105 and 111 may be the same physical device or separate physical devices. In other embodiments, servers 105 and 111 may be hosted by separate or unrelated entities.

FIGS. 2-24B depict exemplary pages corresponding to an application. The application may be personal computer software, a mobile application (e.g., written for the APPLE or ANDROID operating system), or other software that can be executed by a client device 101 or server 105, 111. The exemplary pages may be created by the application in real-time as the application is running, or may be previously stored (e.g., in a memory of a client device 101 or server 105, 111). The data displayed in the pages may likewise be acquired in real-time as the application runs (e.g., acquired from local memory or via a network-connected device through network 103). The data displayed in the pages, and the content of the pages themselves, may change over time. For example, clients 101 may request updates to the data or applications from servers (e.g., server 105 or 111). Similarly, servers 105 or 111 may push updates to client devices 101. Each of the pages may be sent to the client device 101 as a discrete data file (e.g., a single HTML page or single mobile application page), or multiple pages may be sent together to the client 101 in a combined data file. Similarly, an application running on client device 101 or servers 105, 111, may generate pages one-at-a-time or may generate multiple pages that are combined for display.

As further described below in connection with the exemplary pages shown in FIGS. 2-24B, users may interact with the pages in various ways. For example, the pages may include selection areas that users may select using an input device (e.g., capacitive touchscreen, mouse, stylus, etc.), User interactions with the pages may be identified by the client devices 101 and used by an application program running on the client devices 101 and/or on servers 105, 111. User interactions (e.g., selections of selection areas or input of data) may be stored locally on the client device 101 and/or may be sent to server 105 or 111 for storage and/or processing.

Figure 2:
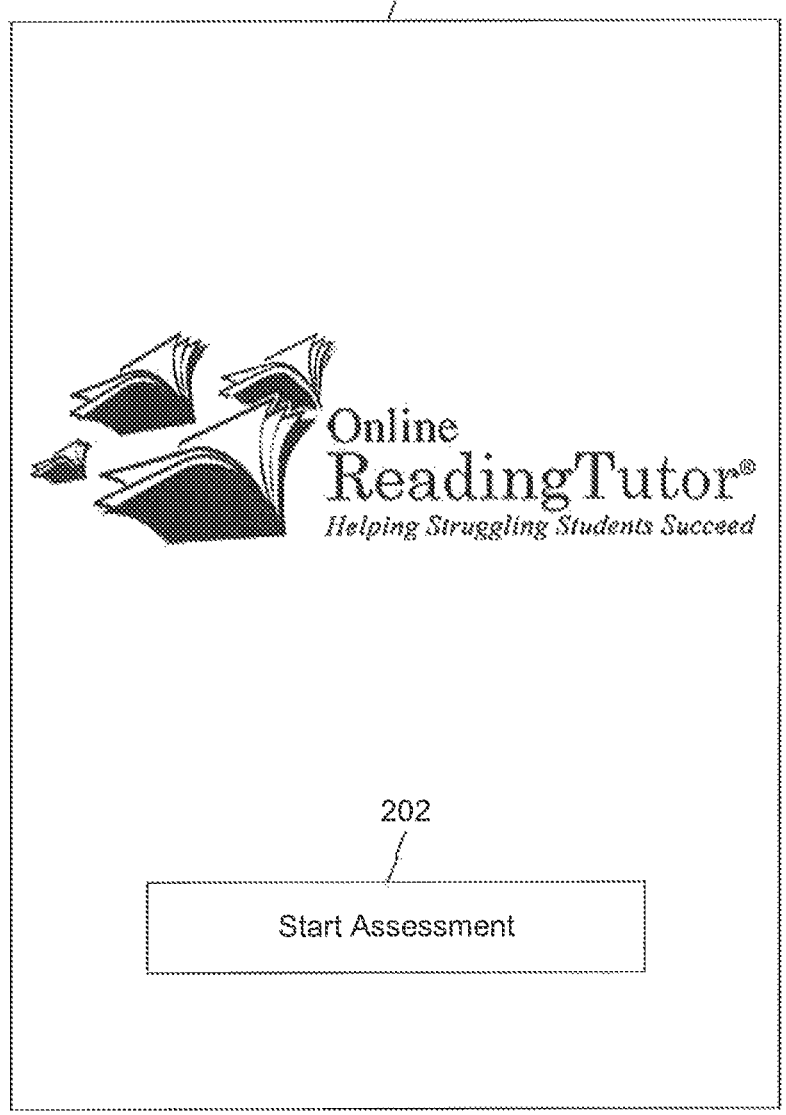
FIG. 2 depicts an exemplary introduction page consistent with embodiments described herein.

FIG. 2 depicts an exemplary introduction page 200. The introduction page may be the first, or one of the first, pages displayed by a client device 101 when an application is being run. As described above, the application may be running on a client device 101 or server, 105, 111. The page 200 may include an area 201, with information about the application, as well as one or more selection areas 202. When selection area 202 is selected, for example, the application may determine to display a further page on the client device 101.

FIG. 3 depicts an exemplary identification page 300. The identification page may include information about the application, as well as an area 302 with information about the next set of slides and nature of the dyslexia screening process. Page 300 may also include fields for the user to enter identifying information 303, such as their name, fields for their grade level 303, and other information.

In some embodiments, pages such as page 300 may be a user interface screen that include fields for entry of textual or other information. Such pages may include virtual buttons (e.g., icons and the like) for entering responses and selecting menu options. Such buttons and other fields may be selected by user input, and thereby activated. As noted above, capacitive touchscreens or other types of touch-sensing devices may be used to receive user selections of icons or buttons. For example, when a user touch is sensed within a particular field of the user interface screen associated with one or more actions, a processing device associated with the client device (or a server) may executed the associated one or more actions. As an example, a user touch sensed within the area of a touch-sensitive display device corresponding to field 303 may trigger a further screen, or page, in which the user can input other information such as their grade level. This description of screens and pages applies generally to such screens and pages described elsewhere herein.

Figure 4:
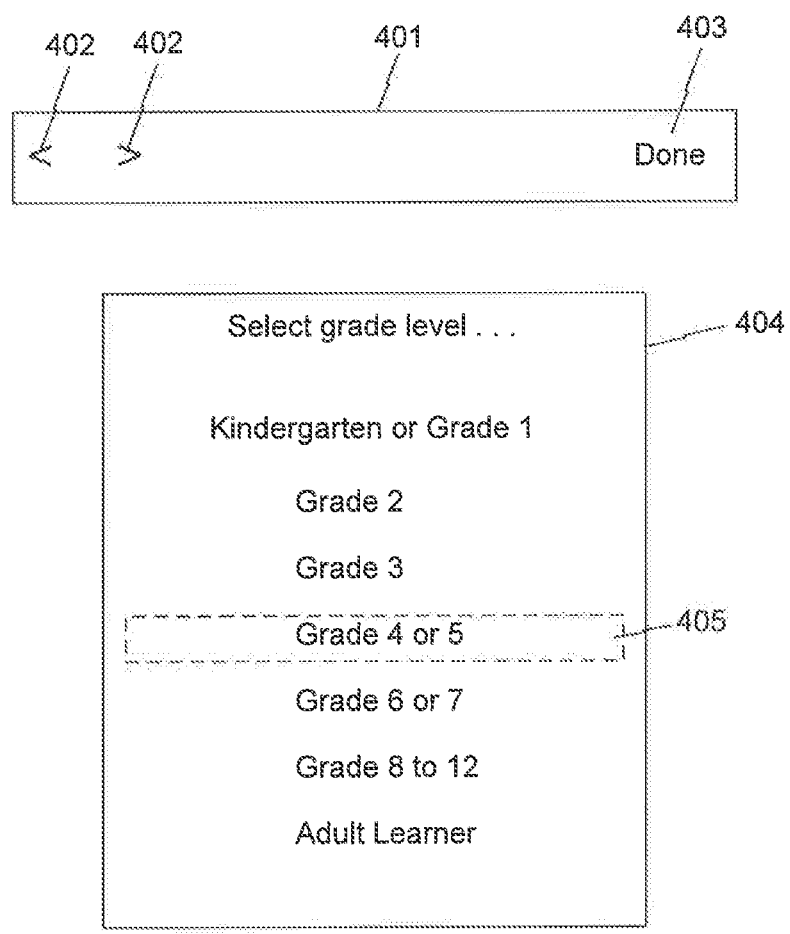
FIG. 4 depicts an exemplary grade selection page consistent with embodiments described herein.

FIG. 4 depicts an exemplary grade selection page 400. Grade selection page 400 may be associated with identification page 300. For example, selection of selection area 303 may cause page 400 to be displayed. Users may navigate through page 400 with selection bar 401, such as by selecting arrows 402, indicating whether the application should display previous or future pages. Users may select their appropriate grade level from selection are 404. In the example shown in FIG. 4, the grade level of Grade 4 or 5 is selected, as shown by the selection box 405. Once a user has selected their grade level, they may select the completion selection area 403, which indicates to the application that the user has selected a grade level. In addition to the grade levels depicted in FIG. 4, other embodiments may use other grade or age levels to classify users.

Figure 5:
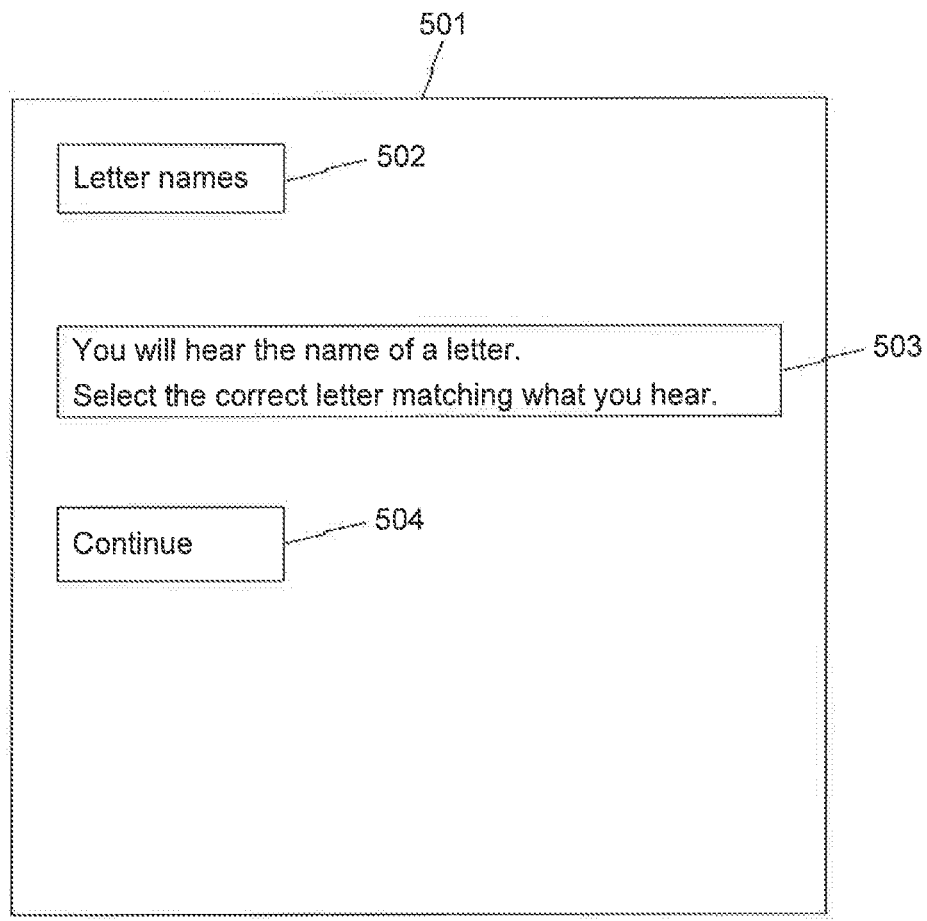
FIG. 5 depicts an exemplary first instruction page consistent with embodiments described herein.

FIG. 5 depicts an exemplary first instruction page 500. Page 500 may include a display area 501 in which instructions regarding the dyslexia screening process are provided. The display area 501 may have a title 502, such as "Letter names." The title may indicate the nature of the dyslexia queries being performed in a specific part of the screening. Instruction area 503 may describe how the user should respond to query screens that are displayed to the user. Selection area 504 may, if selected, cause the application to determine that a next page should be displayed.

Figure 6:
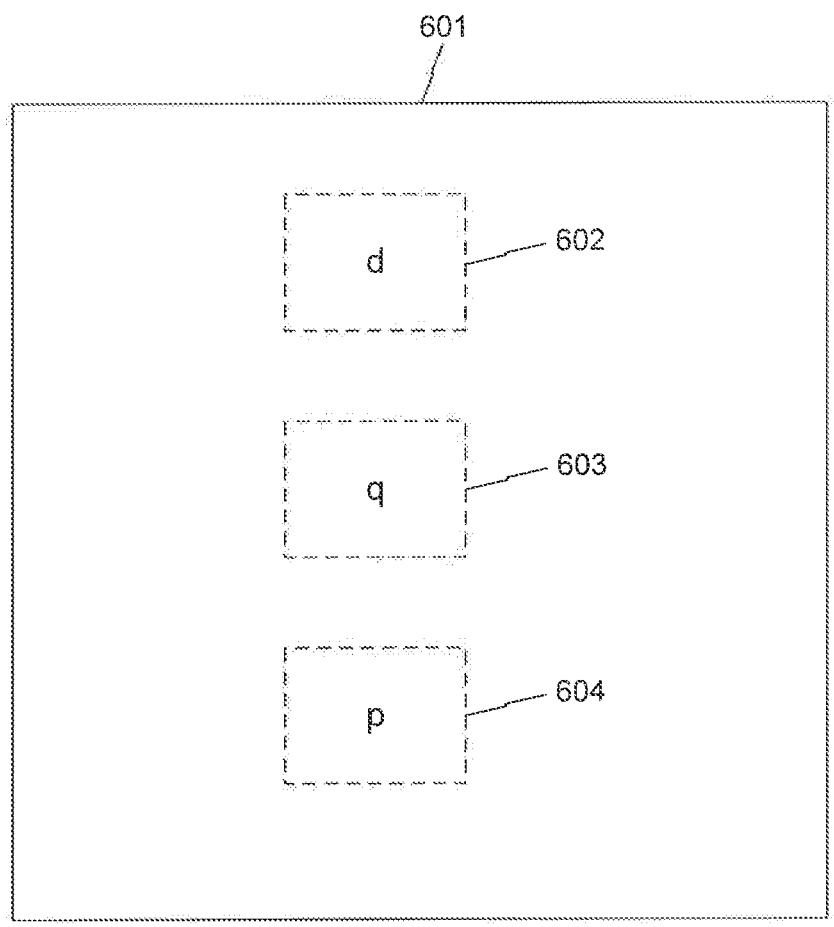
FIG. 6 depicts an exemplary first query page consistent with embodiments described herein.

FIG. 6 depicts an exemplary first query page. The content of the query page 600 may be selected based on the grade level that the user selected (e.g., from pages 300, 400). For example, the difficulty level of the content of the query page 600 may depend on the user's grade level and other information input by the user. With reference to FIG. 1, query page 600 may be sent to the client from database 108 or may be stored locally at the client 101.

Query page 600 may display selection options 602, 603, 604 to the user. For instance, in the example page 600 of FIG. 6, the selection options include the letters "d," "q," and "p." Page 600 may also include information 605 identifying the user's progression through sections of the dyslexia screening, as well as information 606 identifying the user's progression through each section individually. For example, there may be nine sections of the dyslexia screening and twenty queries per section. Other numbers of sections and queries are possible as well.

As query page 600 is displayed on client 101, an auditory query is also rendered by the client. The auditory query may comprise a sound, rendered by a loudspeaker or other audio output of the client 101, corresponding to one of the selection options 602, 603, 604. As indicated in instruction area 503 of page 500, the user should select the correct selection option based on the sound that is rendered. For example, if the auditory query renders a sound of a person saying the letter "p," then the correct response on page 600 would be selection option 604. The auditory query may be rendered once, or multiple times, for a given display of a query page 600.

The auditory query may be rendered using an audio file stored locally at client 101 or remotely from server 105 or 111 (or databases 108 or 109). The auditory query may be associated with one or more query pages. In this way, the auditory query renders a sound corresponding to one of the query options of a query page. In some, but not all embodiments, each auditory query is uniquely associated with a single corresponding query page. The association may be performed by data in a database (e.g., databases 108, 109) linking the auditory query or a sound file with the query page, or by the application running on the client 101 or server 105, 111. The auditory query may be included within a page (e.g., embedded within an HTML page or mobile application page) that is transmitted to a client 101, or may be a separate data file from the page. A sound file corresponding to the auditory query may also be stored at a third-party server (e.g., on a content delivery network), from which the auditory query can be accessed by the client 101.

Each of the pages displayed by a client 101, such as page 600, may function with an associated timer. The timer may generally serve to determine the amount of time (e.g., in seconds) that the user takes to make a selection from selection area 601. Different embodiments may use different starting points for the timer. For example, the starting point may be when a server 105, 111 sends the query page 600 to the client, when the server 105, 111 sends the auditory query to the client, when the client renders the query page 600, when the client renders the auditory query, when the selection area 601 is displayed, when the selection options 602, 603, 604 are displayed, etc. The ending point may likewise differ depending on the embodiment. For example, the ending point may be when the application detects a selection of a selection option 602, 603, 604, when the selection of a selection option is sent to a server 105, 111, when the selection of a selection option is processed by an application on client 101 or server 101, 111, etc. The determined time may be stored for later use, such as use in determining an assessment for the user. The storage may be on the client 101 or a server 105, 111. The same timer, or a different timer, may function to determine how long to display the query page 600. For example, if the timer reaches a predetermined period (e.g., five seconds), the application may transition to the next query page, even if the user has not made a selection on page 600.

Figure 7:
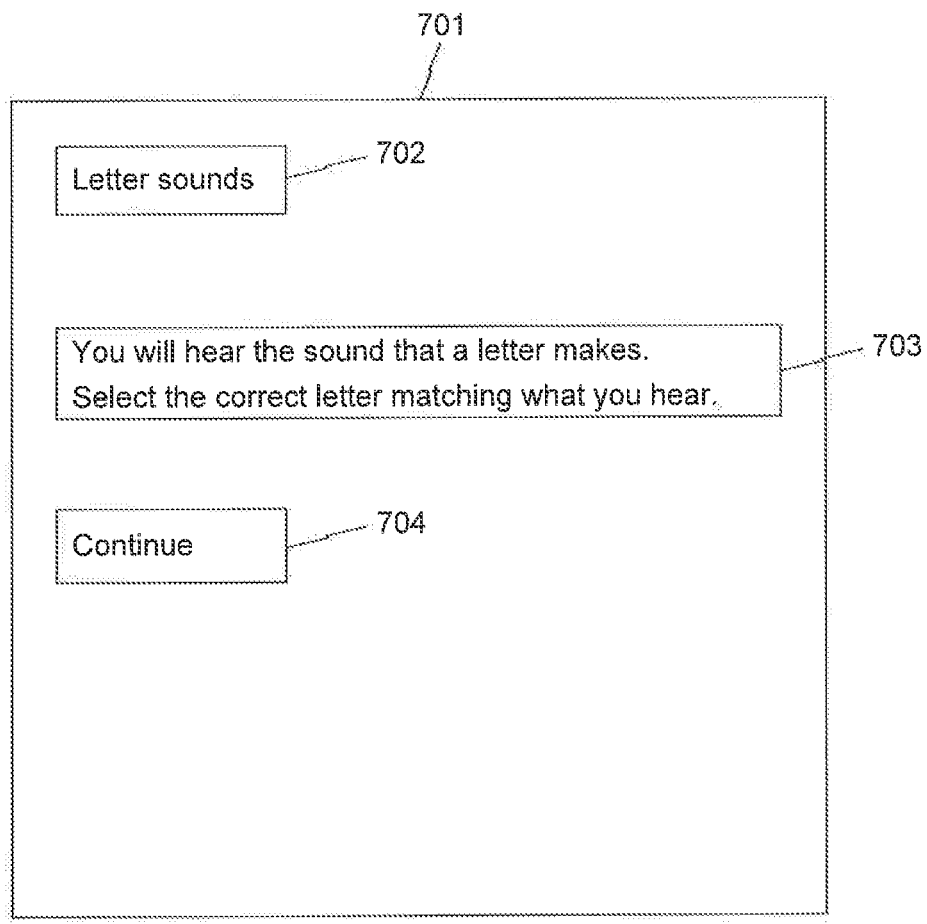
FIG. 7 depicts an exemplary second instruction page consistent with embodiments described herein.

FIG. 7 depicts an exemplary second instruction page 700, which may have features similar to those of the first instruction page 500. Page 700 may include a display area 701 in which instructions regarding the dyslexia screening process are provided. The display area 701 may have a title 702, such as "Letter sounds." The title may indicate the nature of the dyslexia queries being performed in a specific part of the screening. Instruction area 703 may describe how the user should respond to query screens that are displayed to the user. Selection area 704 may, if selected, cause the application to determine that a next page should be displayed.

Figure 8:
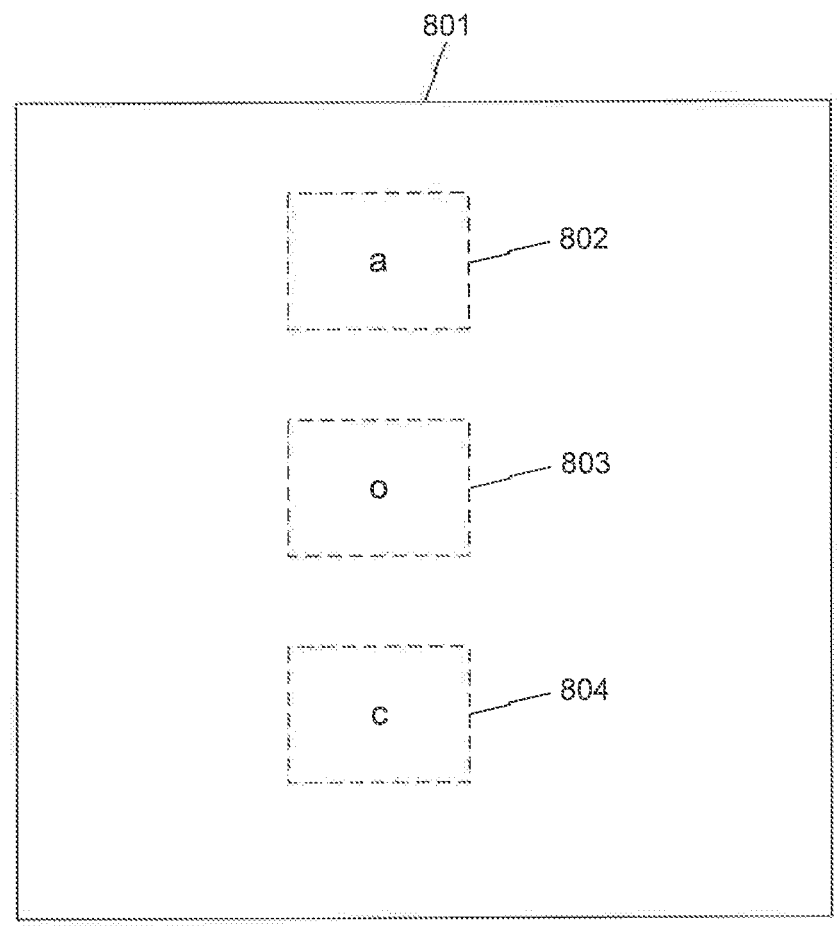
FIG. 8 depicts an exemplary second query page consistent with embodiments described herein.

FIG. 8 depicts an exemplary second query page. Similar to the first query page 600, the content of the query page 800 may be selected based on the grade level that the user selected (e.g., from pages 300, 400). For example, the difficulty level of the content of the query page 800 may depend on the user's grade level and other information input by the user. With reference to FIG. 1, query page 800 may be sent to the client from database 108 or may be stored locally at the client 101.

Query page 800 may display selection options 802, 803, 804 to the user. For instance, in the example page 800 of FIG. 8, the selection options include the letters "a," "o," and "c." Page 800 may also include information 805 identifying the user's progression through sections of the dyslexia screening, as well as information 806 identifying the user's progression through each section individually. For example, there may be nine sections of the dyslexia screening and twenty queries per section. Other numbers of sections and queries are possible as well.

As query page 800 is displayed on client 101 an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 800, may use an associated timer to determine the amount of time (e.g., in seconds) that the user takes to make a selection from selection area 801.

Figure 9:
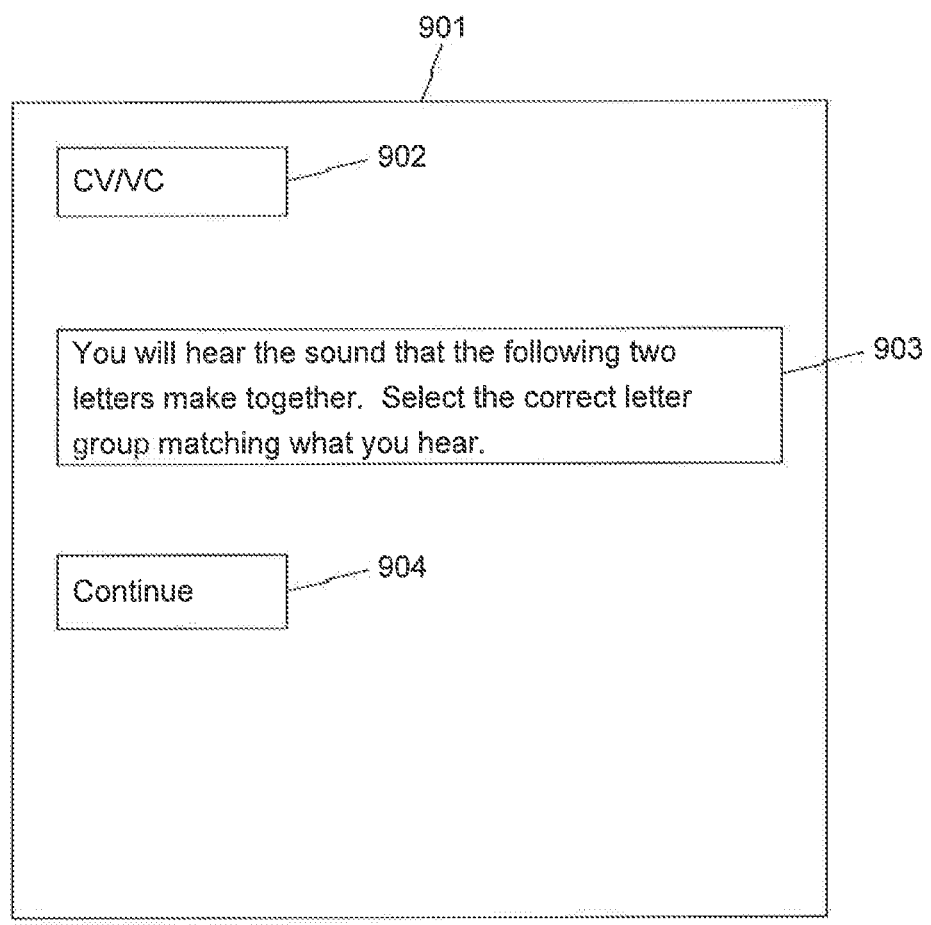
FIG. 9 depicts an exemplary third instruction page consistent with embodiments described herein.

FIG. 9 depicts an exemplary third instruction page 900, which may have features similar to those of the first instruction page 500. Page 900 may include a display area 901 in which instructions regarding the dyslexia screening process are provided. The display area 901 may have a title 902, such as "CV/VC." The title may indicate the nature of the dyslexia queries being performed in a specific part of the screening. Instruction area 903 may describe how the user should respond to query screens that are displayed to the user. Selection area 904 may, if selected, cause the application to determine that a next page should be displayed.

Figure 10:
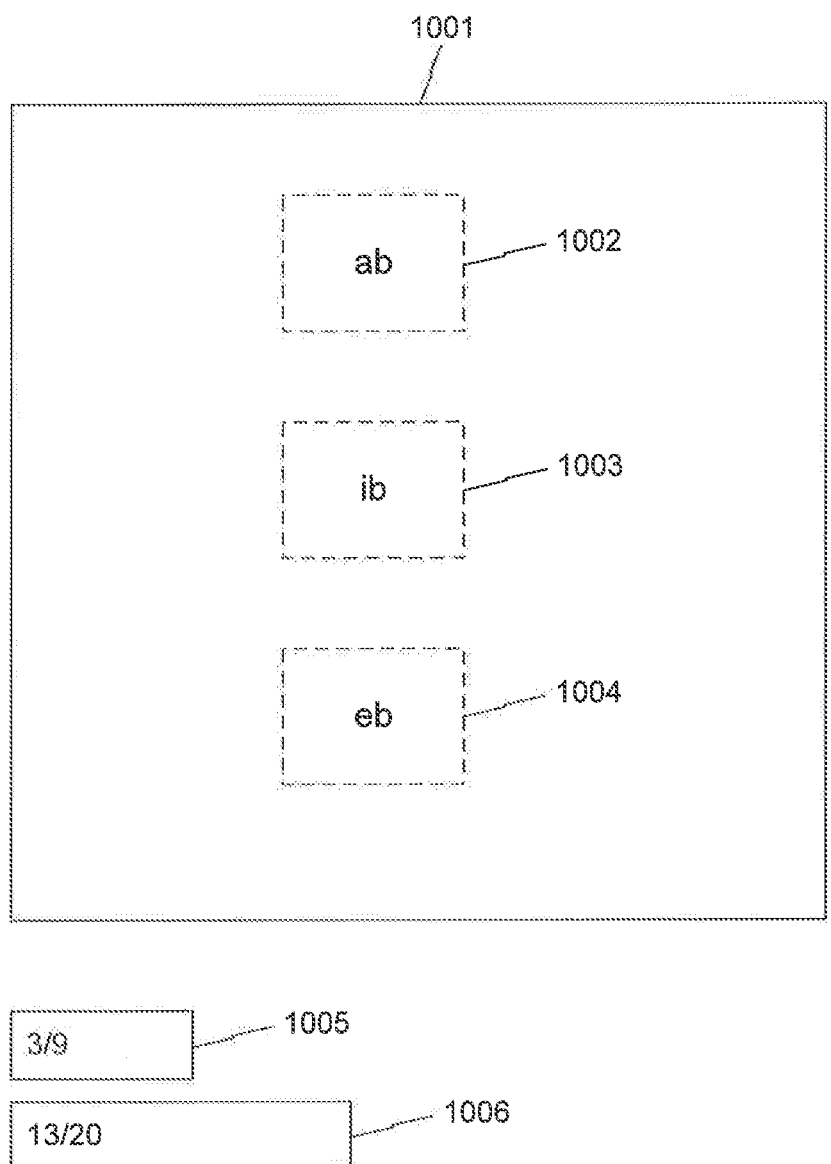
FIG. 10 depicts an exemplary third query page consistent with embodiments described herein.

FIG. 10 depicts an exemplary third query page. Similar to the first query page 600, the content of the query page 1000 may be selected based on the grade level that the user selected (e.g., from pages 300, 400). For example, the difficulty level of the content of the query page 1000 may depend on the user's grade level and other information input by the user. With reference to FIG. 1, query page 1000 may be sent to the client from database 108 or may be stored locally at the client 101.

Query page 1000 may display selection options 1002, 1003, 1004 to the user. For instance, in the example page 1000 of FIG. 10, the selection options include the options "ab," "ib," and "eb." Page 1000 may also include information 1005 identifying the user's progression through sections of the dyslexia screening, as well as information 1006 identifying the user's progression through each section individually. For example, there may be nine sections of the dyslexia screening and twenty queries per section. Other numbers of sections and queries are possible as well.

As query page 1000 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 1000, may use an associated timer to determine the amount of time (e.g., in seconds) that the user takes to make a selection from selection area 1001.

Figure 11:
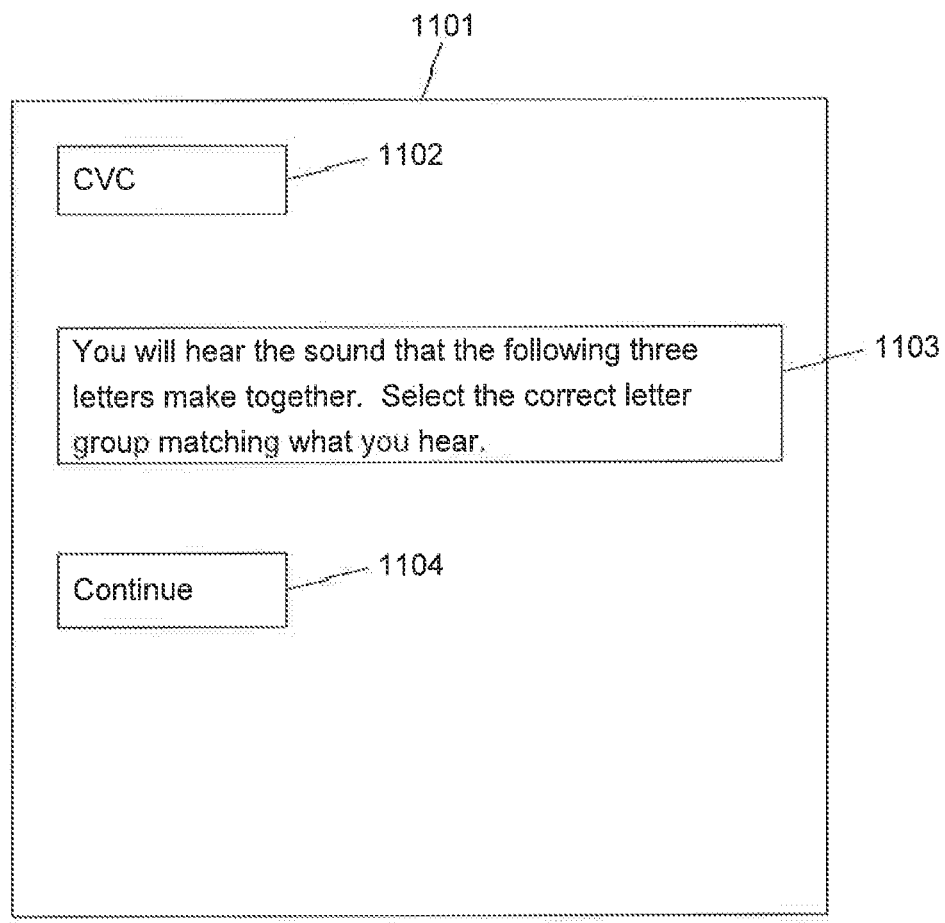
FIG. 11 depicts an exemplary fourth instruction page consistent with embodiments described herein.

FIG. 11 depicts an exemplary fourth instruction page 1100, which may have features similar to those of the first instruction page 500. Page 1100 may include a display area 1101 in which instructions regarding the dyslexia screening process are provided. The display area 1101 may have a title 1102, such as "CVC." The title may indicate the nature of the dyslexia queries being performed in a specific part of the screening. Instruction area 1103 may describe how the user should respond to query screens that are displayed to the user. Selection area 1104 may, if selected, cause the application to determine that a next page should be displayed.

Figure 12:
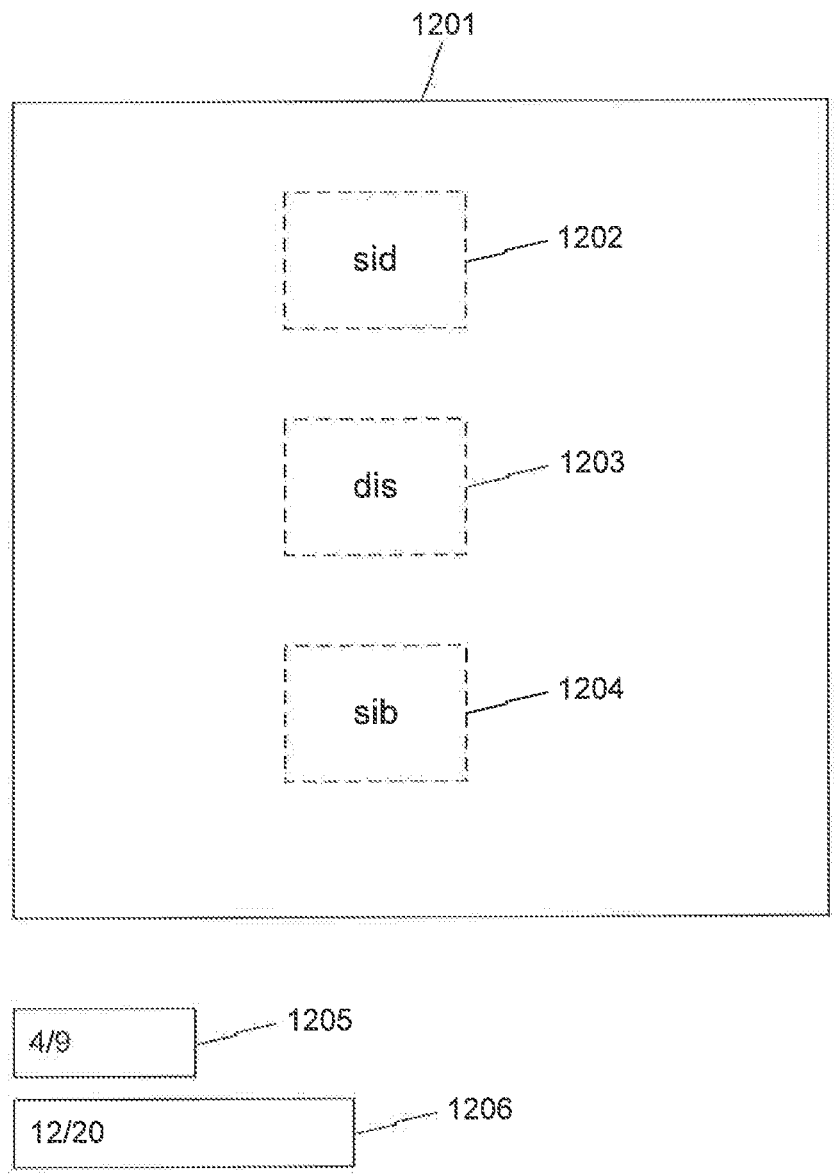
FIG. 12 depicts an exemplary fourth query page consistent with embodiments described herein.

FIG. 12 depicts an exemplary fourth query page. Similar to the first query page 600, the content of the query page 1200 may be selected based on the grade level that the user selected (e.g., from pages 300, 400). For example, the difficulty level of the content of the query page 1200 may depend on the user's grade level and other information input by the user. With reference to FIG. 1, query page 1200 may be sent to the client from database 108 or may be stored locally at the client 101.

Query page 1200 may display selection options 1202, 1203, 1204 to the user. For instance, in the example page 1200 of FIG. 12, the selection options include the options "sid," "dis," and "sib." Page 1200 may also include information 1205 identifying the user's progression through sections of the dyslexia screening, as well as information 1206 identifying the user's progression through each section individually. For example, there may be nine sections of the dyslexia screening and twenty queries per section. Other numbers of sections and queries are possible as well.

As query page 1200 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 1200, may use an associated timer to determine the amount of time (e.g., in seconds) that the user takes to make a selection from selection area 1201.

Figure 13:
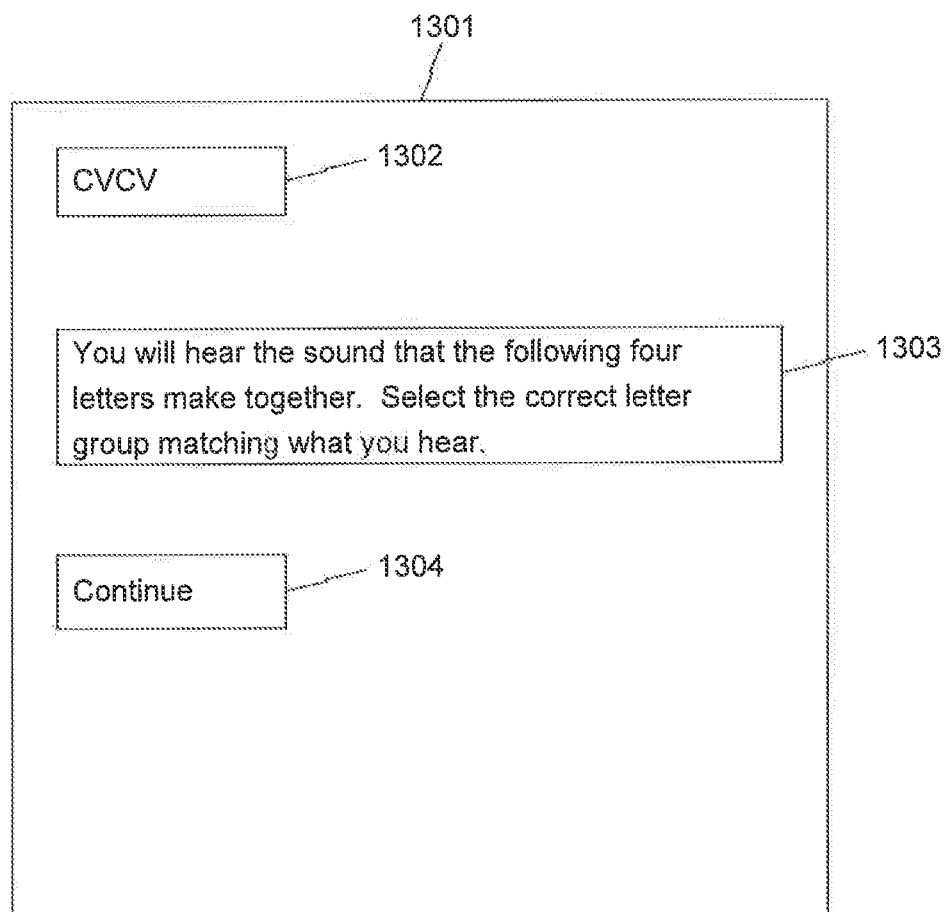
FIG. 13 depicts an exemplary fifth instruction page consistent with embodiments described herein.

FIG. 13 depicts an exemplary fifth instruction page 1300, which may have features similar to those of the first instruction page 500. Page 1300 may include a display area 1301 in which instructions regarding the dyslexia screening process are provided. The display area 1301 may have a title 1302, such as "CVCV." The title may indicate the nature of the dyslexia queries being performed in a specific part of the screening. Instruction area 1303 may describe how the user should respond to query screens that are displayed to the user. Selection area 1304 may, if selected, cause the application to determine that a next page should be displayed.

Figure 14:
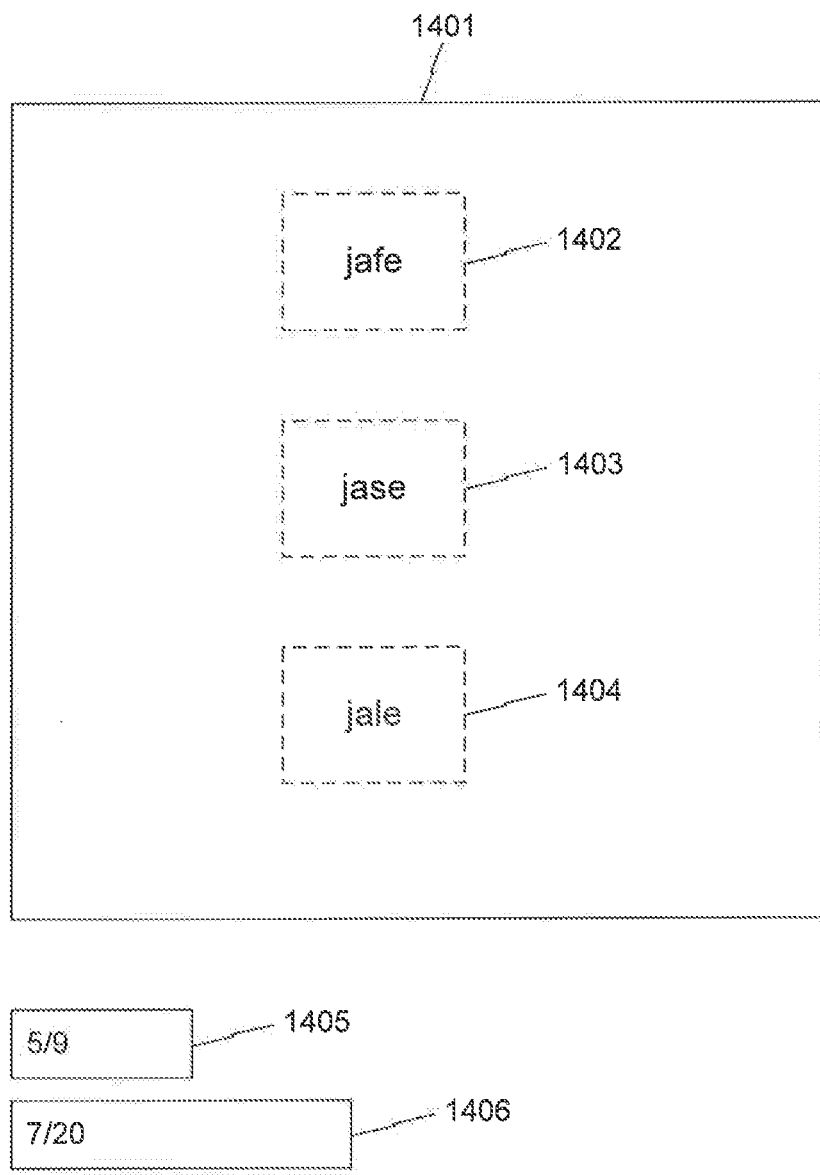
FIG. 14 depicts an exemplary fifth query page consistent with embodiments described herein.

FIG. 14 depicts an exemplary fifth query page. Similar to the first query page 600, the content of the query page 1400 may be selected based on the grade level that the user selected (e.g., from pages 300, 400). For example, the difficulty level of the content of the query page 1400 may depend on the user's grade level and other information input by the user. With reference to FIG. 1, query page 1400 may be sent to the client from database 108 or may be stored locally at the client 101.

Query page 1400 may display selection options 1402, 1403, 1404 to the user. For instance, in the example page 1400 of FIG. 144, the selection options include the options "jafe," "jase," and "jale." Page 1400 may also include information 1405 identifying the user's progression through sections of the dyslexia screening, as well as information 1406 identifying the user's progression through each section individually. For example, there may be nine sections of the dyslexia screening and twenty queries per section. Other numbers of sections and queries are possible as well.

As query page 1400 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 1400, may use an associated timer to determine the amount of time (e.g., in seconds) that the user takes to make a selection from selection area 1401.

Figure 15:
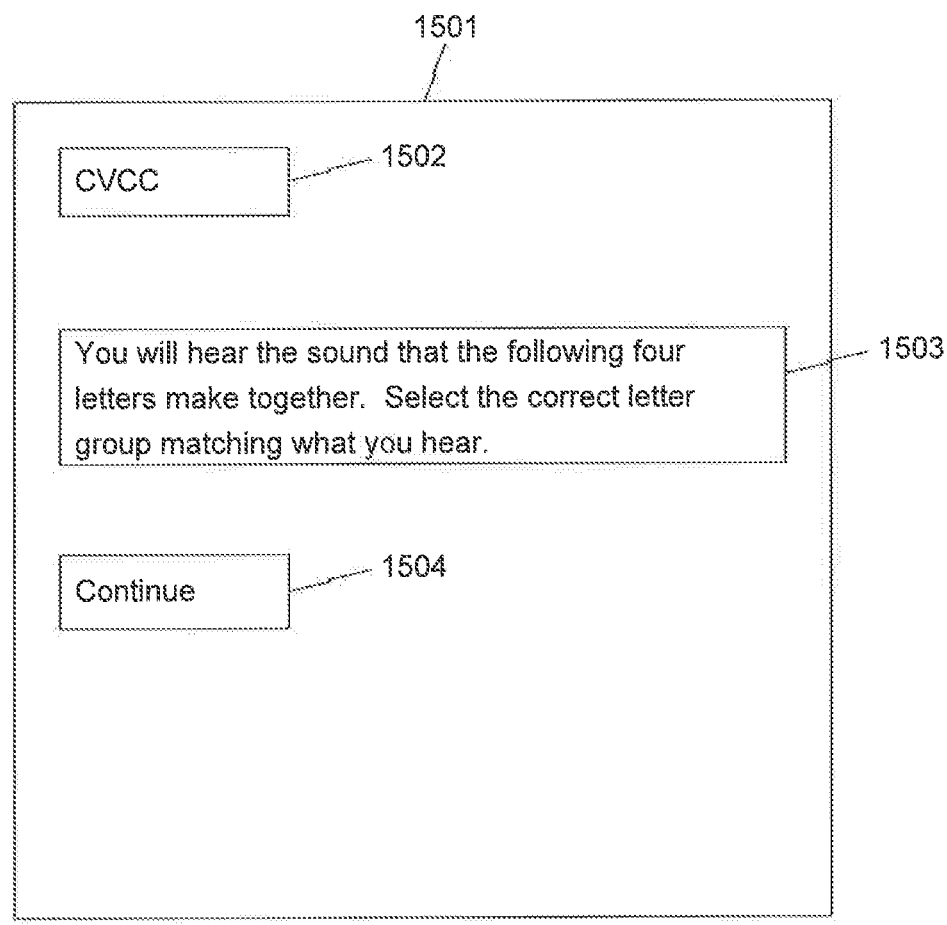
FIG. 15 depicts an exemplary sixth instruction page consistent with embodiments described herein.

FIG. 15 depicts an exemplary sixth instruction page 1500, which may have features similar to those of the first instruction page 500. Page 1500 may include a display area 1501 in which instructions regarding the dyslexia screening process are provided. The display area 1501 may have a title 1502, such as "CVCC." The title may indicate the nature of the dyslexia queries being performed in a specific part of the screening. Instruction area 1503 may describe how the user should respond to query screens that are displayed to the user. Selection area 1504 may, if selected, cause the application to determine that a next page should be displayed.

Figure 16:
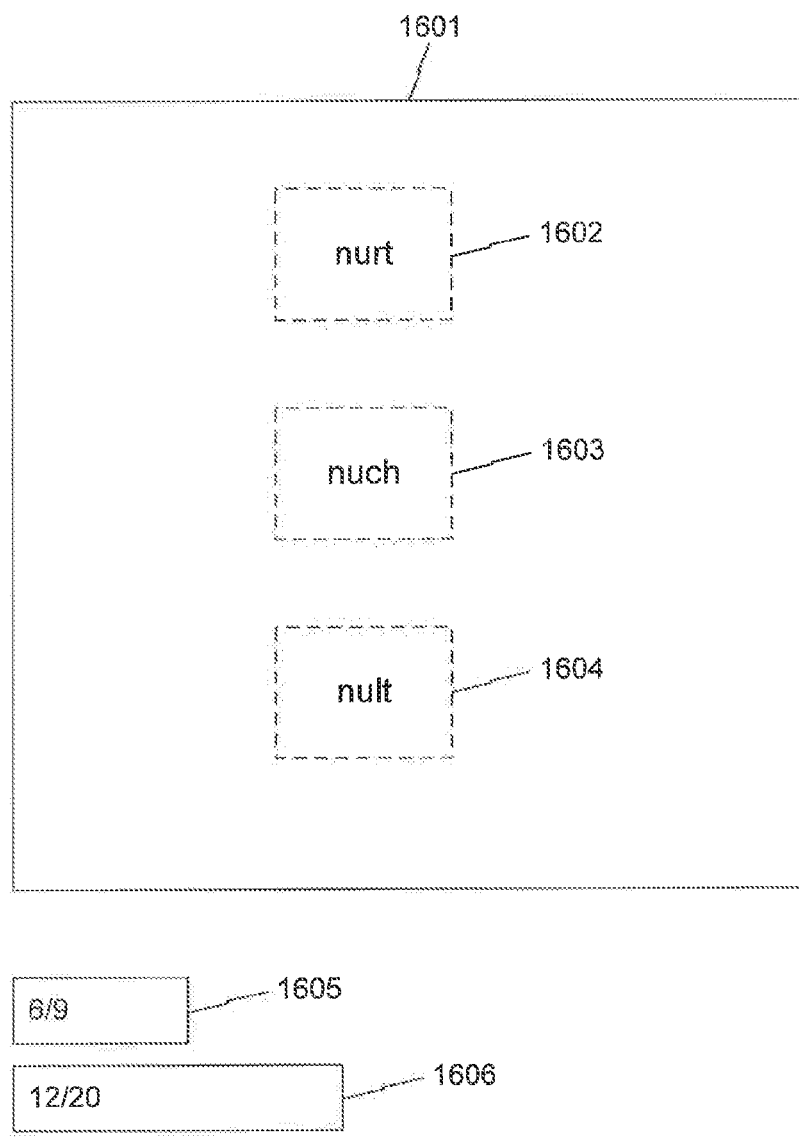
FIG. 16 depicts an exemplary sixth query page consistent with embodiments described herein.

FIG. 16 depicts an exemplary sixth query page. Similar to the first query page 600, the content of the query page 1600 may be selected based on the grade level that the user selected (e.g., from pages 300, 400). For example, the difficulty level of the content of the query page 1600 may depend on the user's grade level and other information input by the user. With reference to FIG. 1, query page 1600 may be sent to the client from database 108 or may be stored locally at the client 101.

Query page 1600 may display selection options 1602, 1603, 1604 to the user. For instance, in the example page 1600 of FIG. 16, the selection options include the options "nurt," "nuch," and "nult." Page 1600 may also include information 1605 identifying the user's progression through sections of the dyslexia screening, as well as information 1606 identifying the user's progression through each section individually. For example, there may be nine sections of the dyslexia screening and twenty queries per section. Other numbers of sections and queries are possible as well.

As query page 1600 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 1600, may use an associated timer to determine the amount of time (e.g., in seconds) that the user takes to make a selection from selection area 1601.

Figure 17:
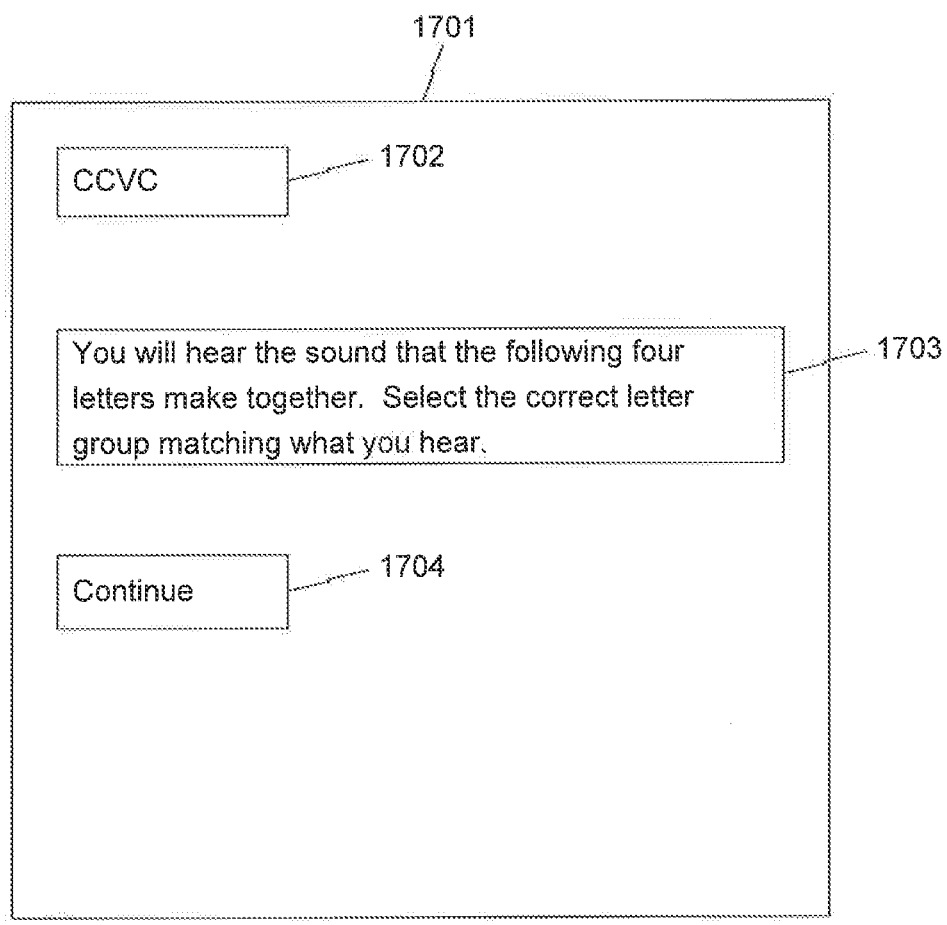
FIG. 17 depicts an exemplary seventh instruction page consistent with embodiments described herein.

FIG. 17 depicts an exemplary seventh instruction page 1700, which may have features similar to those of the first instruction page 500. Page 1700 may include a display area 1701 in which instructions regarding the dyslexia screening process are provided. The display area 1701 may have a title 1702, such as "CCVC sounds." The title may indicate the nature of the dyslexia queries being performed in a specific part of the screening. Instruction area 1703 may describe how the user should respond to query screens that are displayed to the user. Selection area 1704 may, if selected, cause the application to determine that a next page should be displayed.

Figure 18:
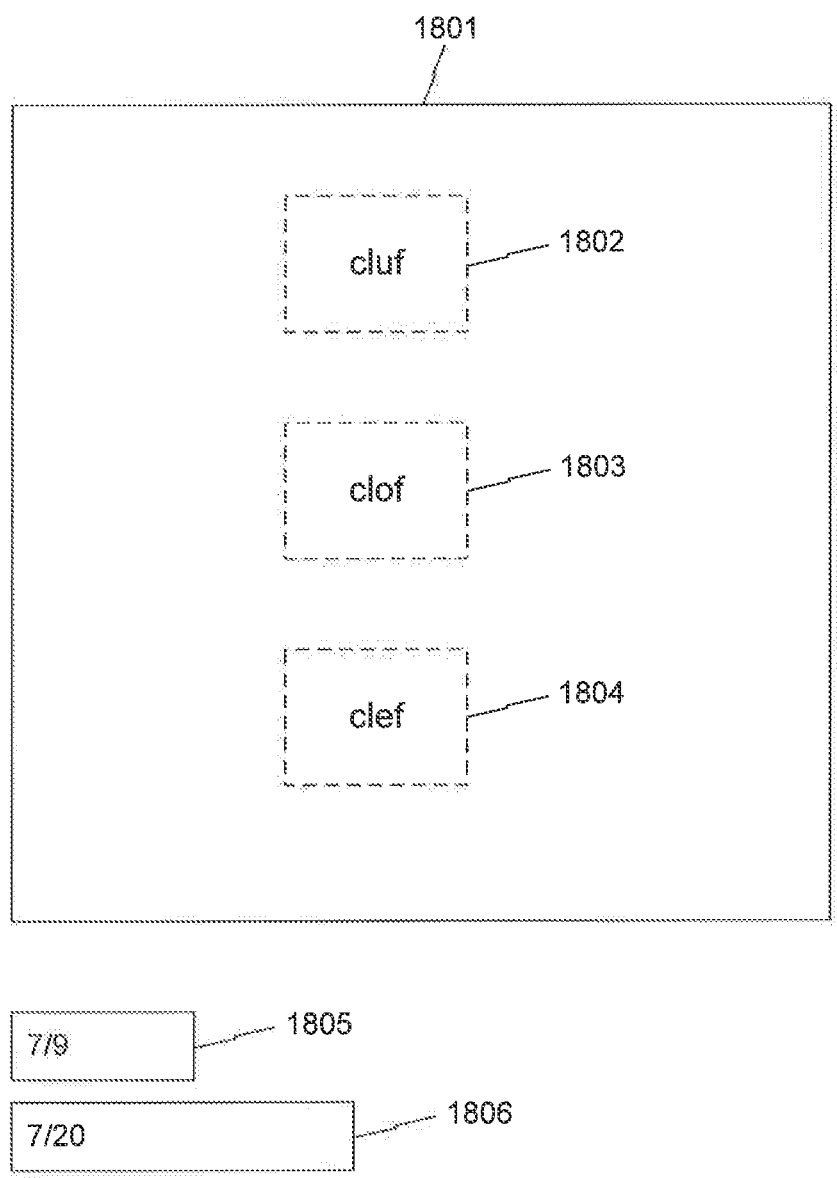
FIG. 18 depicts an exemplary seventh query page consistent with embodiments described herein.

FIG. 18 depicts an exemplary seventh query page. Similar to the first query page 600, the content of the query page 1800 may be selected based on the grade level that the user selected (e.g., from pages 300, 400). For example, the difficulty level of the content of the query page 1800 may depend on the user's grade level and other information input by the user. With reference to FIG. 1, query page 1800 may be sent to the client from database 108 or may be stored locally at the client 101.

Query page 1800 may display selection options 1802, 1803, 1804 to the user. For instance, in the example page 1800 of FIG. 18, the selection options include the options "cluf," "clof," and "clef." Page 1800 may also include information 1805 identifying the user's progression through sections of the dyslexia screening, as well as information 1806 identifying the user's progression through each section individually. For example, there may be nine sections of the dyslexia screening and twenty queries per section. Other numbers of sections and queries are possible as well.

As query page 1800 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 1800, may use an associated timer to determine the amount of time (e.g., in seconds) that the user takes to make a selection from selection area 1801.

Figure 19:
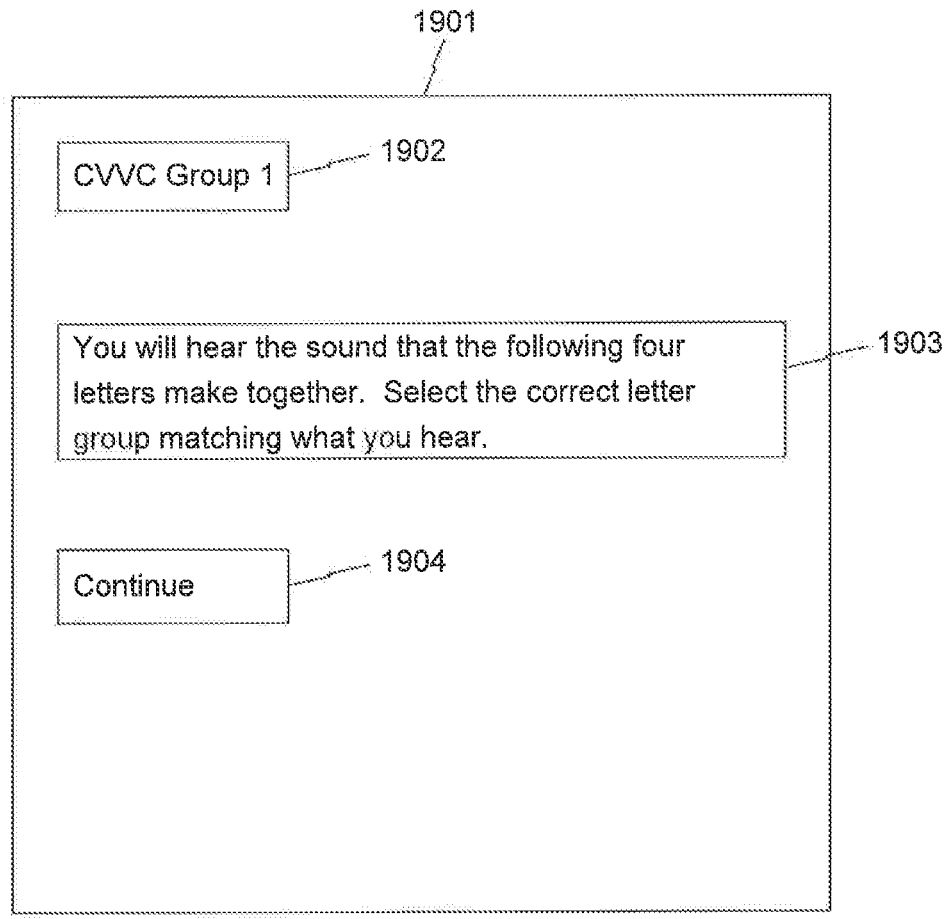
FIG. 19 depicts an exemplary eighth instruction page consistent with embodiments described herein.

FIG. 19 depicts an exemplary eighth instruction page 1900, which may have features similar to those of the first instruction page 500. Page 1900 may include a display area 1901 in which instructions regarding the dyslexia screening process are provided. The display area 1901 may have a title 1902, such as "CVVC Group 1." The title may indicate the nature of the dyslexia queries being performed in a specific part of the screening. Instruction area 1903 may describe how the user should respond to query screens that are displayed to the user. Selection area 1904 may, if selected, cause the application to determine that a next page should be displayed.

Figure 20:
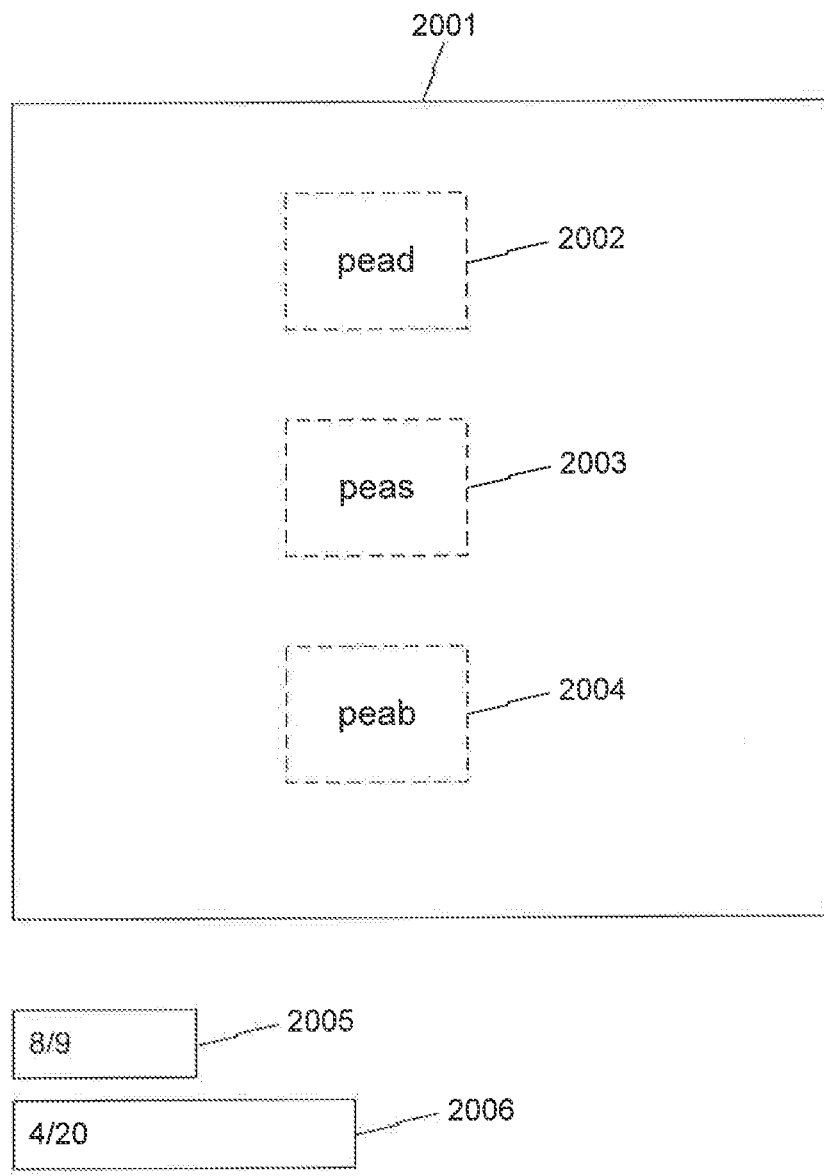
FIG. 20 depicts an exemplary eighth query page consistent with embodiments described herein.

FIG. 20 depicts an exemplary eighth query page. Similar to the first query page 600, the content of the query page 2000 may be selected based on the grade level that the user selected (e.g., from pages 300, 400). For example, the difficulty level of the content of the query page 2000 may depend on the user's grade level and other information input by the user. With reference to FIG. 1, query page 2000 may be sent to the client from database 108 or may be stored locally at the client 101.

Query page 2000 may display selection options 2002, 2003, 2004 to the user. For instance, in the example page 2000 of FIG. 20, the selection options include the options "pead," "peas," and "peab." Page 2000 may also include information 2005 identifying the user's progression through sections of the dyslexia screening, as well as information 2006 identifying the user's progression through each section individually. For example, there may be nine sections of the dyslexia screening and twenty queries per section. Other numbers of sections and queries are possible as well.

As query page 2000 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 2000, may use an associated timer to determine the amount of time (e.g., in seconds) that the user takes to make a selection from selection area 2001.

Figure 21:
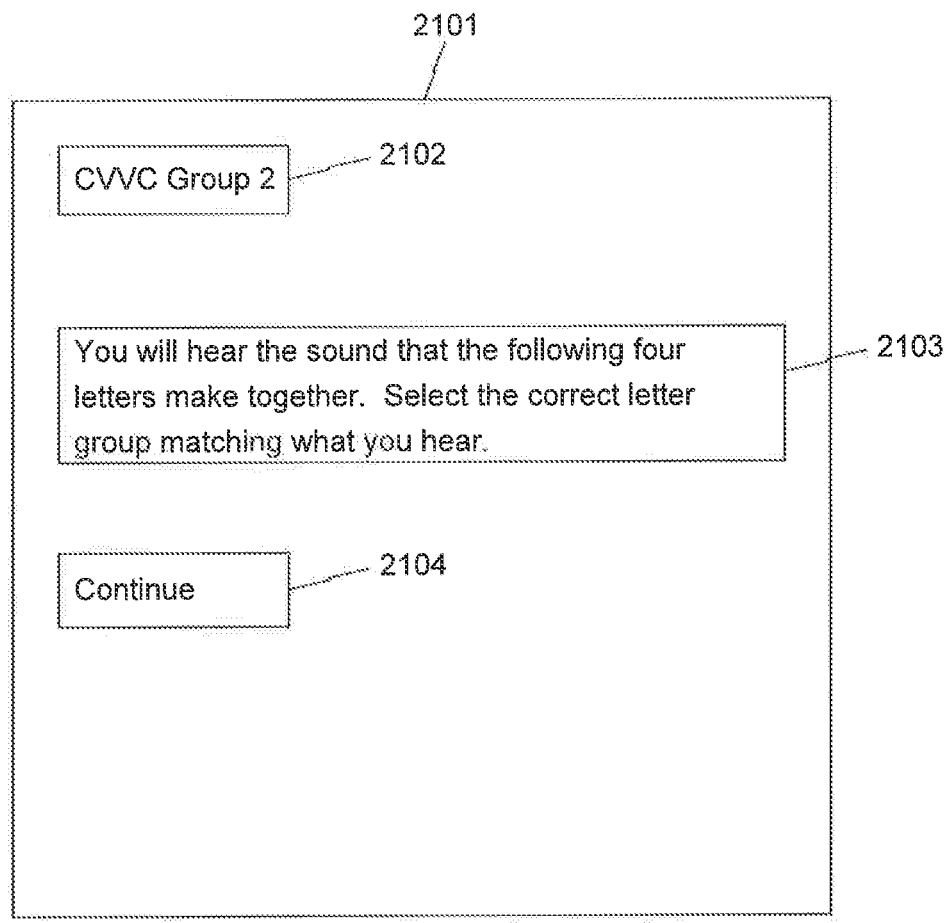
FIG. 21 depicts an exemplary ninth instruction page consistent with embodiments described herein.

FIG. 21 depicts an exemplary ninth instruction page 2100, which may have features similar to those of the first instruction page 500. Page 2100 may include a display area 2101 in which instructions regarding the dyslexia screening process are provided. The display area 2101 may have a title 2102, such as "CVVC Group 2." The title may indicate the nature of the dyslexia queries being performed in a specific part of the screening. Instruction area 2103 may describe how the user should respond to query screens that are displayed to the user. Selection area 2104 may, if selected, cause the application to determine that a next page should be displayed.

Figure 22:
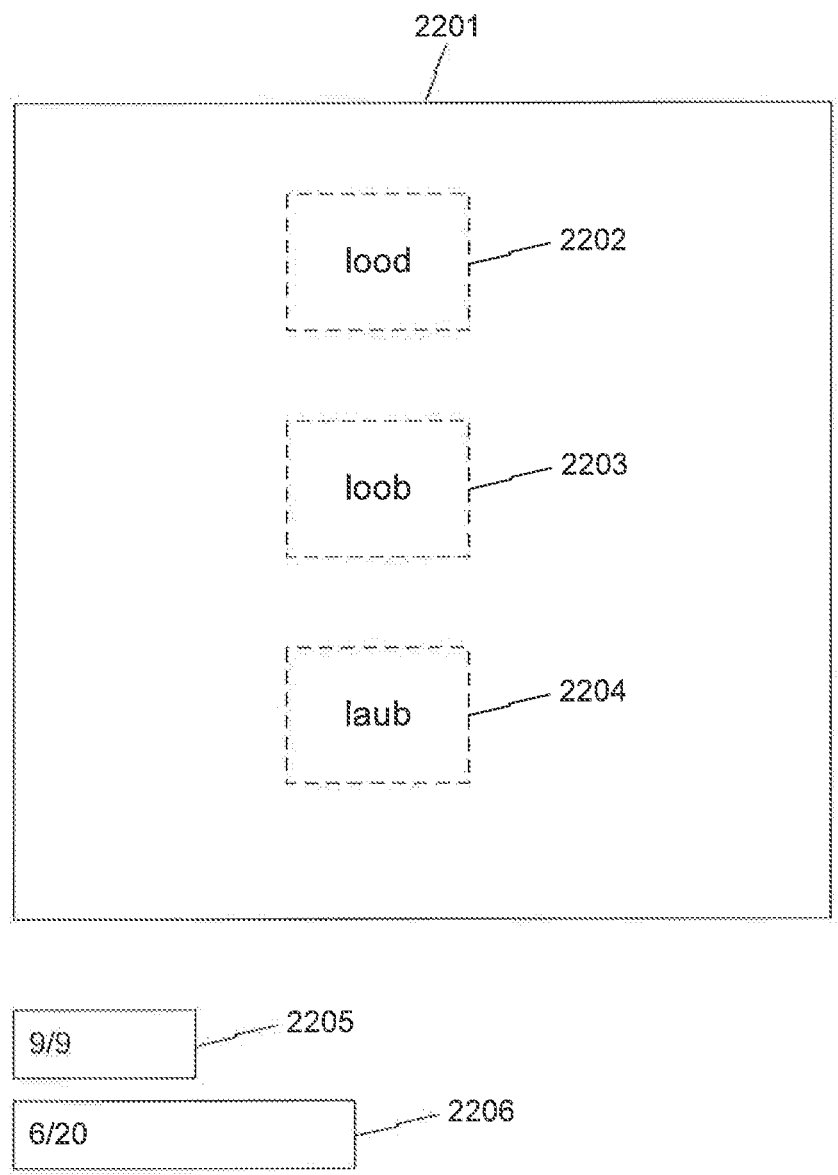
FIG. 22 depicts an exemplary ninth query page consistent with embodiments described herein.

FIG. 22 depicts an exemplary ninth query page. Similar to the first query page 600, the content of the query page 2200 may be selected based on the grade level that the user selected (e.g., from pages 300, 400). For example, the difficulty level of the content of the query page 2200 may depend on the user's grade level and other information input by the user. With reference to FIG. 1, query page 2200 may be sent to the client from database 108 or may be stored locally at the client 101.

Query page 2200 may display selection options 2202, 2203, 2204 to the user. For instance, in the example page 2200 of FIG. 22, the selection options include the options "lood," "loob," and "laub." Page 2200 may also include information 2205 identifying the user's progression through sections of the dyslexia screening, as well as information 2206 identifying the user's progression through each section individually. For example, there may be nine sections of the dyslexia screening and twenty queries per section. Other numbers of sections and queries are possible as well.

As query page 2200 is displayed on client 101, an auditory query is also rendered by the client, similar to the rendering of the auditory queries discussed above in connection with query page 600. As with the auditory query discussed above, the auditory query may be rendered using an audio file stored locally at client 101 or remotely from server 105 or 111 (or databases 108 or 109). Further, as discussed above, each of the pages displayed by a client 101, such as page 2200, may use an associated timer to determine the amount of time (e.g., in seconds) that the user takes to make a selection from selection area 2201.

FIG. 23 depicts an exemplary assessment page. Page 2300 may include a section 2301 with a title, such "Assessment Complete," indicating that the query process has completed. A field 2302 may indicate the minimum expected accuracy for a user within the age category selected by the user. For example, for the age group "Grade 4 or 5," an accuracy of 94% may be considered the average or median. This typical accuracy may be determined by an experienced educator familiar with the application and the content of the query pages. In other embodiments, the accuracy may be determined based on historical usage data of the application. For example, the typical accuracy may be an average or median of the accuracy scores actually obtained by users of the application.

As discussed above, the user of a timer in connection with the query pages may influence the accuracy scores of users. For example, a predetermined amount of time may be set as a threshold time for each query page. In some embodiments, if the user takes more than the threshold time (T seconds) to select a response from the query page, the user's answer may be deemed incorrect. In addition, in some embodiments, if more than T seconds passes (or another predetermined length of time different than T seconds), the next query page in a set of query pages may be displayed, even if the user has not made a selection from the query page being displayed. In some embodiments, thresholds may be used to select a weight for a user's scores based on how long they take to respond to queries. For example, if the user responds between 0 and $T_1$ seconds, the user's response (if correct) may be given 100% weight (e.g., a score of 1). If the user responds between $T_1$ and $T_2$ seconds, the user's response (if correct) may be given 50% weight (e.g., a score of 0.5). If the user responds after $T_2$ seconds, their response (even if correct) may be given no weight. Other weighting and scoring techniques can be used as well.

Page 2300 may also include a field 2303 indicating the user's name, to give the page 2300 a personalized appearance. A field 2304 may indicate the accuracy of the user's responses to the query pages included in a dyslexia assessment. For example, the accuracy may be based on the user's responses to the query page, with or without adjustments to their raw scores based on a timer, as discussed above. Page 2300 may also include an explanation area 2305, explaining the typical accuracy rate for individuals of a comparable age group. Area 2305 may also provide information describing how the user may submit information from their assessment to a service provider. Selection option 2306 may allow the user to restart the dyslexia screening process. If selected, option 2306 may cause the application to display the same query pages and auditory queries (in the same or a different sequence), or different query pages and auditory queries. Selection option 2307 allows the user to continue with a process of submitting information to a service provider.

Page 2300 may also indicate the types, and prevalence, of certain types of errors in a user's responses to query pages. For example, instances of phonetic and mirror image errors may be identified. Phonetic errors may occur when a user is unable to match a sound that they hear to a pattern of letters that they see. For example, if the user hears "sid" from page 1200 in FIG. 12, selection of "sib" would be a phonetic error. Mirror image errors may occur when a user identifies an incorrect answer that is a mirror image of a correct answer. For example, on page 1200 of FIG. 1200, if a user hears "sid," selection of "dis" would be a mirror image error.

Figure 24B:
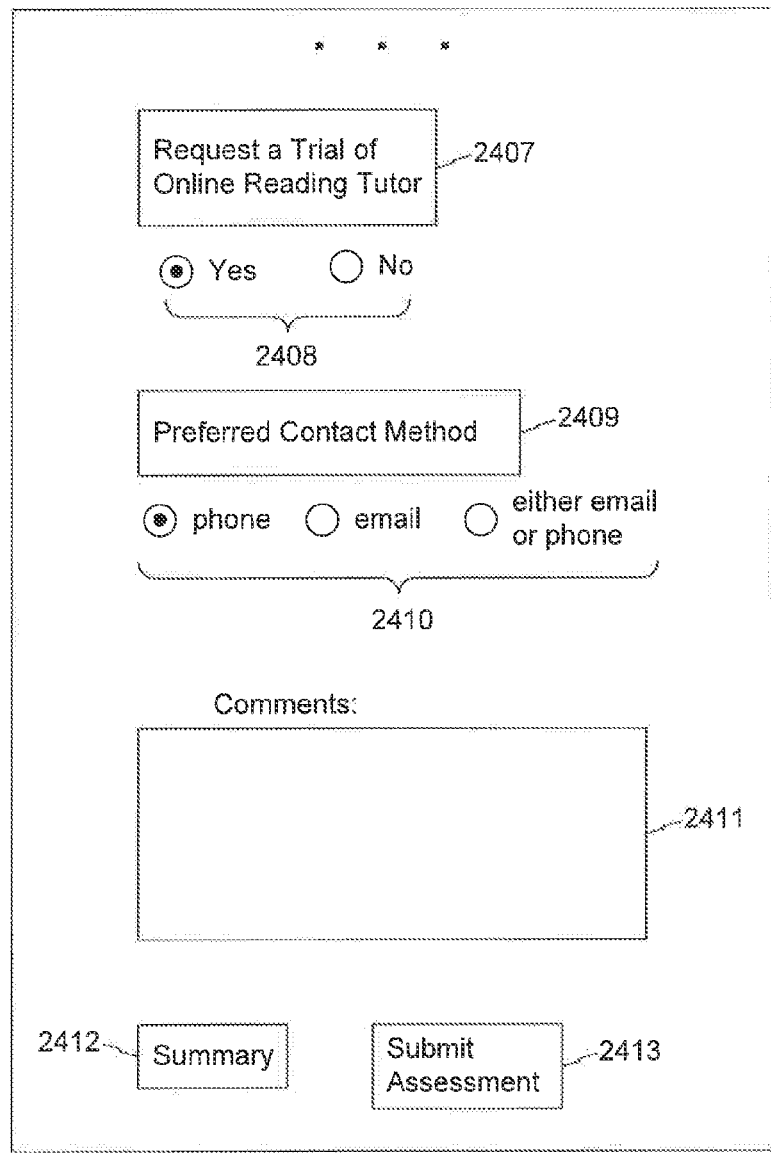
FIG. 24B depicts an exemplary second feedback page consistent with embodiments described herein.

FIG. 24A depicts an exemplary first feedback page. The page 2400 may include an area 2401 that allows the user to input their name (selection area 2402), telephone number (selection area 2403), email address (selection area 2404), country of residence (selection area 2405), and status (e.g., as a parent, teacher, or student) (selection areas 2406). Further, FIG. 24B depicts an exemplary second feedback page, which may also be part of page 2400. Page 2400 may include an area 2407, allowing the user to request a trial of dyslexia education software or personal instruction. Selection options 2408 may indicate whether such a trial is desired by the user. Area 2409 allows the user to indicate their preferred contact method, using selection options 2410. Comment field 2411 may allow the user to type comments regarding the dyslexia assessment, or other topics, that may be sent to a service provider. Selection option 2412 may display a summary of the information entered by the user. Selection option 2413 may submit the information to a service provider (e.g., a company hosting the application or another company).

Figure 25:
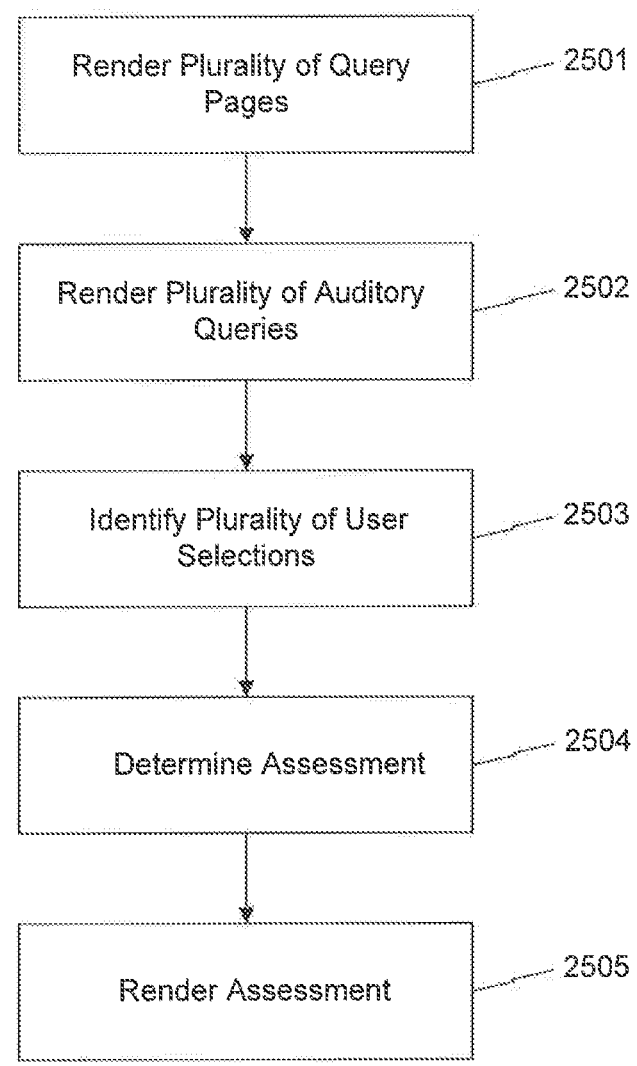
FIG. 25 depicts an exemplary flowchart corresponding to a first process for detecting dyslexia consistent with embodiments described herein.

FIG. 25 depicts an exemplary flowchart corresponding to a first process for detecting dyslexia. Process 2500 may include a step 2501, in which a plurality of query pages may be rendered. The query pages may, for example, be downloaded to a client device 101 or may be running on a server 105, 111 and displayed to a client 101. In either case, the query pages may be downloaded or displayed one-by-one, or in a group, depending on the embodiment. The pages may be rendered using hardware and software of the client, such as a graphics card, display screen, and associated software.

In a step 2502, a plurality of auditory queries may be rendered. As discussed above, the auditory queries may correspond to the query pages. The auditory queries may be included in the query pages or may be separate data files. Further, as discussed above, the auditory queries may be stored locally at a client device 101 or at a server 105, 111 and rendered on a client 101.

In a step 2503, a plurality of user selections may be identified. As discussed above, the selections may be made using a client device (e.g., via a capacitive touchscreen, stylus, mouse, etc.). The user selections may be stored locally at the client 101 or remotely at a server 105, 111. Similarly, the user selections may be processed locally or remotely. For each user selection, the application running on the client 101, or on server 105, 111, may identify which field(s) were selected by the user.

In a step 2504, an assessment may be determined. As discussed above, an assessment (e.g., accuracy score) may be calculated based on a user's responses to query pages, with or without taking into account the time it took the user to respond to queries. The assessment may be received at the client 101 and rendered, in a step 2505, on the client 101. For example, an assessment page, such as that shown in FIG. 23, may be displayed on the client 101. Other graphical display options may be used as well.

Figure 26:
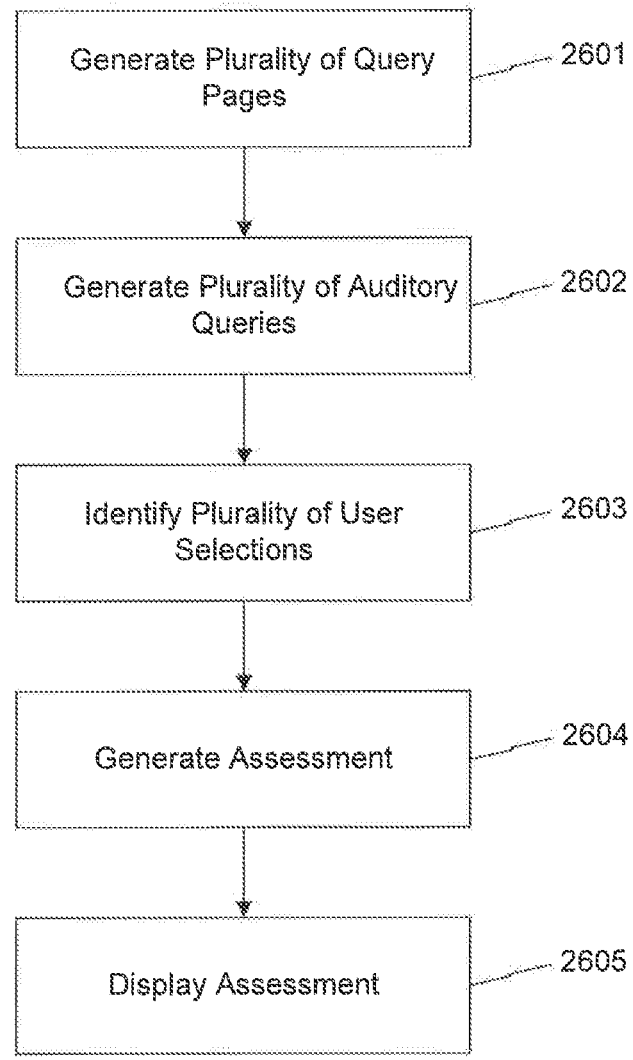
FIG. 26 depicts an exemplary flowchart corresponding to a second process for detecting dyslexia consistent with embodiments described herein.

FIG. 26 depicts an exemplary flowchart corresponding to a second process for detecting dyslexia. Process 2600 may include a step 2601 of generating a plurality of query pages 2601. As discussed above, the pages may be generated at a server, such as servers 105, 111 and transmitted to a client 101. In some embodiments, the application running on a client 101 or server 105, 111 may generate the query page. For example, the application may access data (stored locally or at a database 108, 109, 112) to build each query page, including its selection options, and to render a corresponding auditory query.

In a step 2602, a plurality of auditory queries may be generated. As discussed above, the auditory queries may be generated together with the query pages or in separate data files. The auditory queries may be stored locally at the client 101 or remotely at a server 105, 111. The auditory queries may be rendered at the client 101 as each query page is displayed on the client 101.

In a step 2603, a plurality of user selections may be identified. The selections may be identified as a user selects a selection option from a query page corresponding to the auditory query that is rendered. The identification of the selections may be performed by the application running on the client 101 or server 105, 111, or may be identified at a server 105, 111 with a separate application.

In a step 2604, an assessment may be generated. For example, in some embodiments a page similar to the page depicted in FIG. 23 may be generated. The page may be generated by the client application or by the server 105, 111. As discussed above, the assessment may include an accuracy score indicating the user's accuracy of responses to the query pages and auditory queries. The score may or may not take into account the time it took the user to respond to each query.

Figure 27:
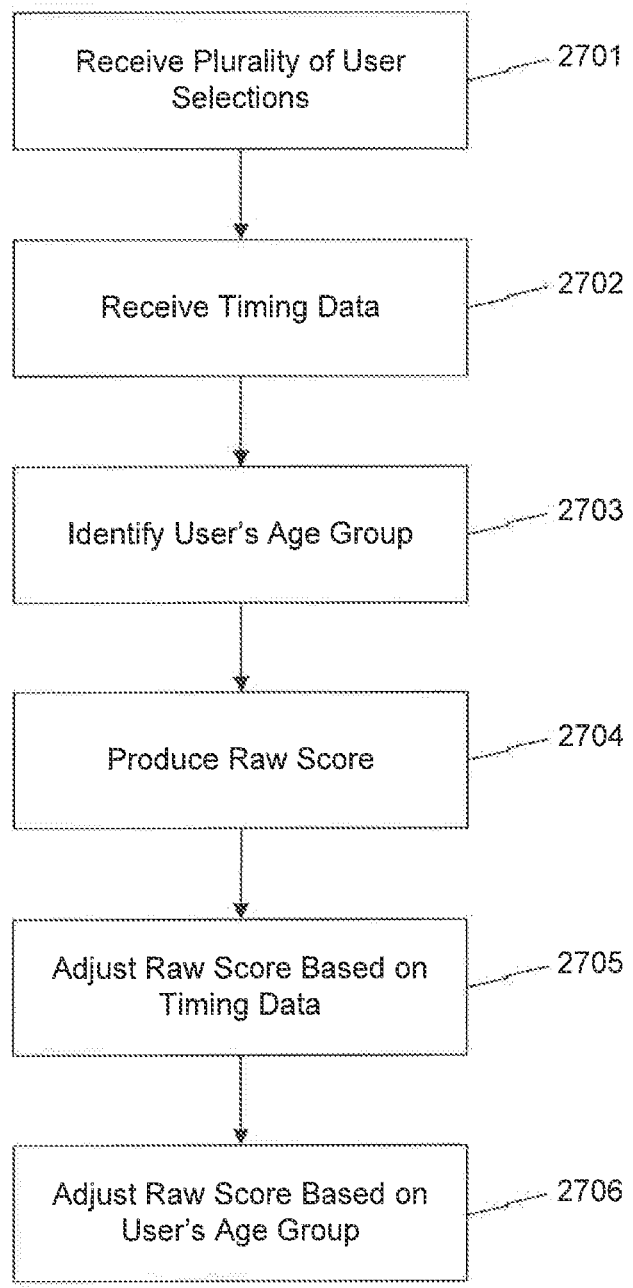
FIG. 27 depicts an exemplary flowchart corresponding to a process for generating an assessment consistent with embodiments described herein.

FIG. 27 depicts an exemplary process 2700 for generating an assessment based on a dyslexia screening process. The assessment, as discussed above, may indicate a user's accuracy of responses to a series of queries in a dyslexia screening process.

In a step 2701, a plurality of user selections may be received. This step, as discussed above, may occur locally at the client 101 or remotely at a server 105, 111. The user selections may indicate which selection options from query pages were selected by a user. As discussed above, the user selections may be stored locally at the client 101 or remotely at a server 105, 111.

In a step 2702, timing data may be received. The timing data, as discussed above, may indicate an amount of time (e.g., in seconds) that a user took to respond to a query page. The timing data may be received on a query-by-query basis, or may be received as an aggregate group of time data records. The timing data may be stored, and received, either at client 101 or server 105, 111.

In a step 2703, the user's age group may be identified. This information may come from user input, such as a grade level selected from the pages shown in FIGS. 3 and 4.

In a step 2704, a raw score may be calculated based on the user's responses to queries. For example, if an assessment was performed in which nine sets of twenty queries were presented to a user, user response data would exist for 180 individual queries. Step 2704 may involve determining the number, or percentage, of the queries that the user answered correctly.

In a step 2705, the raw score may be adjusted based on timing data. For example, if a user answered 170 queries correctly, but exceeded a time threshold for five of the queries, their adjusted score may be 165. As discussed above, weights may also be applied to query responses to account for how long a user took to respond to queries.

In a step 2706, the raw score may also be adjusted based on a user's age group. For example, in embodiments where the user's assessment is displayed in the form of a relative score (e.g., how well the user performed compared to other users of similar ages), the raw score may be adjusted up or down by a certain number or percentage.

Systems and methods consistent with the present disclosure enable a detection of a user's risk for dyslexia to be performed. The functionality of the dyslexia detection process can be easily extended to include additional and different functionality as well.

The above described systems and methods are exemplary and are not intended to be limiting. For purposes of explanation only, certain aspects of the present disclosure are described herein with reference to the components illustrated in the figures. The functionality of the illustrated components may overlap, however, and may be present in a fewer or greater number of elements and modules. Further, all or part of the functionality of the illustrated elements may coexist or be distributed among several geographically dispersed locations. Moreover, embodiments, features, aspects, and principles of the present invention may be implemented in various environments and are not limited to the illustrated environments.

Further, the sequences of steps shown in or described in connection with the figures are exemplary and not intended to be limiting. Thus, other method steps may be used, and even with the methods depicted in the figures the particular order of events may vary without departing from the scope of the present invention. Moreover, certain steps may not be present and additional steps may be implemented. Also, the processes described herein are not inherently related to any particular apparatus and may be implemented by any suitable combination of components.

The foregoing description of possible implementations consistent with the present disclosure does not represent a comprehensive list of all such implementations or all variations of the implementations described. The description of only some implementations should not be construed as an intent to exclude other implementations. Artisans will understand how to implement the invention in the appended claims in many other ways, using equivalents and alternatives that do not depart from the scope of the following claims. Moreover, unless indicated to the contrary in the preceding description, none of the components described in the implementations are essential to the invention.

What is claimed is:

1. A computer-implemented method comprising a plurality of software operations, each software operation being performed using at least one network-connected computer-based system, the method determining a user's risk of dyslexia and comprising:

identifying, based on an input received from an input device of the computer-based system, an age category associated with the user;

rendering, on a display screen of the computer-based system, a plurality of query pages, each query page being generated from data received by the computer-based system from a remote server over a data communications channel and stored in a memory device of the computer-based system, and each query page comprising a plurality of non-verbal answers that are determined based on the identified age category and are selectable by the user;

rendering, via a speaker of the computer-based system, a plurality of auditory queries, each auditory query being rendered as audible sounds and generated from a sound data file corresponding to a non-verbal query, each auditory query being associated with one or more of the plurality of query pages;

identifying, via the input device of the computer-based system, a plurality of electronic input selections from the user, each electronic input selection identifying a non-verbal answer from a query page;

identifying, via a timer of the computer-based system, timing data associated with the plurality of electronic input selections, the timing data indicating time intervals between the rendering of each of the plurality of auditory queries and the detection of electronic input selections from the user corresponding to each of the auditory queries;

assigning weighted scores to each of the electronic input selections from the user, the weighted scores being determined based on the identified age category and the time intervals, wherein time intervals above a first threshold receive a first weighting factor and time intervals below the first threshold receive a second weighting factor; and rendering, on the display screen of the computer-based system, an assessment in a graphical user interface, the assessment identifying a risk of dyslexia for the user based on whether the weighted scores exceed a predefined threshold associated with the plurality of query pages.

2. The computer-implemented method of claim 1, further comprising:

determining a difficulty level based on the identified age category associated with the user; and selecting the plurality of query pages, the first and second weighting factors, and the plurality of auditory queries based on the determined difficulty level.

3. The computer-implemented method of claim 1, wherein the timing data is calculated in real-time separately for each of the plurality of query pages.

4. The computer-implemented method of claim 1, wherein the assessment identifies phonetic errors based on the selections.

5. The computer-implemented method of claim 1, wherein the assessment identifies mirror image errors based on the selections.

6. The computer-implemented method of claim 1, wherein identifying the plurality of electronic input selections from the user comprises receiving the plurality of electronic input selections via a touch-sensitive display of the computer-based system.

7. The computer-implemented method of claim 1, further comprising, each time no selection from the user is identified within a second threshold, changing a query page that is being rendered on the display screen of the computer-based system, wherein the second threshold is different from the first threshold.

8. The computer-implemented method of claim 7, further comprising determining that the user made an incorrect electronic input selection of a non-verbal answer from a query page each time no electronic input selection from the user is identified within the second threshold.

9. The computer-implemented method of claim 1, wherein the timing data is used to select the first and second weighting factors from a plurality of available weighting factors.

10. A computer-readable medium comprising a plurality of software instructions that, when executed by at least one network-connected computer-based system, perform a method of determining a user's risk of dyslexia, the instructions comprising:
   instructions for identifying, based on an input received from an input device of the computer-based system, an age category associated with the user;
   instructions for generating a plurality of query pages, each query page being generated from data received by the computer-based system from a remote server over a data communications channel and stored in a memory device of the computer-based system, and each query page comprising a plurality of non-verbal answers that are determined based on the identified age category and are selectable by the user;
   instructions for generating a plurality of auditory queries to be rendered via a speaker of the computer-based system, each auditory query being producible as audible sounds and generated from a sound data file corresponding to a non-verbal query, each auditory query being associated with one or more of the plurality of query pages;
   instructions for identifying, via the input device of the computer-based system, a plurality of electronic input selections from the user, each electronic input selection identifying a non-verbal answer from a query page;
   instructions for identifying, via a timer of the computer-based system, timing data associated with the plurality of electronic input selections, the timing data indicating time intervals between the rendering of each of the plurality of auditory queries and the detection of electronic input selections from the user corresponding to each of the auditory queries;
   instructions for assigning weighted scores to each of the electronic input selections from the user, the weighted scores being determined based on the identified age category and the time intervals, wherein time intervals above a first threshold receive a first weighting factor and time intervals below the first threshold receive a second weighting factor; and
   instructions for rendering, on the display screen of the computer-based system, an assessment in a graphical user interface, the assessment identifying a risk of dyslexia for the user based on whether the weighted scores exceed a predefined threshold associated with the plurality of query pages.

11. The computer-readable medium of claim 10, further comprising:
   instructions for determining a difficulty level based on the identified age category associated with the user; and
   instructions for selecting the plurality of query pages, the first and second weighting factors, and the plurality of auditory queries based on the determined difficulty level.

12. The computer-readable medium of claim 10, wherein the timing data is calculated in real-time separately for each of the plurality of query pages.

13. The computer-readable medium of claim 10, wherein the assessment identifies phonetic errors based on the selections.

14. The computer-readable medium of claim 10, wherein the assessment identifies mirror image errors based on the selections.

15. The computer-readable medium of claim 10, further comprising instructions for receiving the plurality of electronic input selections via a touch-sensitive display of the computer-based system.

16. The computer-readable medium of claim 10, further comprising instructions for, each time no selection from the user is identified within a second threshold, changing a query page that is being rendered on the display screen of the computer-based system, wherein the second threshold is different from the first threshold.

17. The computer-readable medium of claim 16, further comprising instructions for determining that the user made an incorrect electronic input selection of a non-verbal answer from a query page each time no electronic input selection from the user is identified within the second threshold.

18. The computer-readable medium of claim 10, wherein the timing data is used to select the first and second weighting factors from a plurality of available weighting factors.

* * * * *